(12) United States Patent (10) Patent No.: US 8,697,381 B2
Radhakrishna et al. (45) Date of Patent: Apr. 15, 2014

(54) METHODS FOR IDENTIFYING MODULATORS OF RGS21 ACTIVITY, COMPOSITIONS COMPRISING AN RGS21 MODULATOR, AND METHODS OF USE THEREOF TO MODULATE TASTE SENSATION

(75) Inventors: Harish Radhakrishna, Tucker, GA (US); Michael D. Brown, Lilburn, GA (US); Grant Dubois, Roswell, GA (US)

(73) Assignee: The Coca-Cola Company, Atlanta, GA (US)

( * ) Notice: Subject to any disclaimer, the term of this patent is extended or adjusted under 35 U.S.C. 154(b) by 880 days.

(21) Appl. No.: 11/828,904

(22) Filed: Jul. 26, 2007

(65) Prior Publication Data

US 2008/0039534 A1 Feb. 14, 2008

Related U.S. Application Data

(60) Provisional application No. 60/820,426, filed on Jul. 26, 2006.

(51) Int. Cl.
*C12Q 1/50* (2006.01)

(52) U.S. Cl.
USPC ................................................ 435/17; 435/21

(58) Field of Classification Search
USPC ........................................................ 435/17, 21
See application file for complete search history.

(56) References Cited

PUBLICATIONS

Snow et al, "GTPase Activating Specificity of RGS12 and Binding Specificity of an Alternatively Spliced PDZ (PSD-95/Dlg/ZO-1) Domain," (The Journal of Biological Chemistry), Jul. 10, 1998, vol. 273, No. 28,pp. 17749-17755.*
Ouyang et al. "Regulators of G-protein signaling 4, insertion into model membranes and inhibition of activity by phosphatidic acid", JBC, 2003, 278(13):11115-11122.*
Adler et al., 2000, "A Novel Family of Mammalian Taste Receptors," Cell 100:693-702.
Berman et al., 1996, "GAIP and RGS4 are GTPase-Activating Proteins for the Gi Subfamily of G Protein a Subunits," Cell 86:445-52.
Bufe et al., 2002, "The Human TAS2R16 Receptor Mediates Bitter Taste in Response to B-Glucopyranosides," Nat. Genet. 32:397-401.
Chandrashekar et al., 2000, "T2Rs Function as Bitter Taste Receptors," Cell 100:703-11.
DeVries et al., 2000, "The Regulator of G Protein Signaling Family," Ann. Rev. Pharmacol. 40:235.
Hunt et al., 1996, "RGS10 is a Selective Activator of G Alpha i GTPase Activity," Nature 383:175-77.
Li et al., 2002, "Human Receptors for Sweet and Umami Taste," Proc. Natl. Acad. Sci. USA 99(7):4692-96.
Lindemann, 1996, "Taste Reception," Physiol. Rev. 76:718-66.
Nelson et al., 2001, "Mammalian Sweet Taste Receptors," Cell 106:381-90.
Nelson et al., 2002, "An Amino-Acid Taste Receptor," Nature 416:199-202.
Neubig et al., 2002, "Regulators of G-Protein Signalling as New Central Nervous System Drug Targets," Nat. Rev. Drug Discov. 1(3):187-97.
Ross et al., 2001, Ann. Rev. Biochem. 69:795.
von Buchholtz, et al., 2004, "RGS21 is a Novel Regulator of G Protein Signalling Selectively Expressed in Subpopulations of Taste Bud Cells," European Journal of Neuroscience, 19:1535-1544.
Watson et al., 1996, "RGS Family Members: GTPase-Activating Proteins for Heterotrimeric G-Protein alpha-Subunits," Nature, 383:172-75.
Zhang et al., 2003, "Coding of Sweet, Bitter, and Umami Tastes: Different Receptor Cells Sharing Similar Signaling Pathways," Cell 112:293-301.
Zhao et al., 2003, "The Receptors for Mammalian Sweet and Umami Taste," Cell 115:255-66.
Zhong et al., 2001, "Regulator of G Protein Signaling Proteins: Novel Multifunctional Drug Targets," J. Pharmacol. Exp. Ther. 297(3):837-45.

* cited by examiner

*Primary Examiner* — Bin Shen
(74) *Attorney, Agent, or Firm* — King & Spalding

(57) ABSTRACT

The present invention provides methods for identifying compounds that selectively and specifically modulate RGS21 gene expression, RGS21 protein expression, and/or the interaction of RGS21 with G proteins in taste signal transduction. In particular, the present invention provides methods for identifying modulators of RGS21 activity for enhancing sweet taste, or other taste perception. Compositions comprising modulators of RGS21 activity for modulating taste signaling transduction are also provided.

9 Claims, 3 Drawing Sheets

METHODS FOR IDENTIFYING MODULATORS OF RGS21 ACTIVITY, COMPOSITIONS COMPRISING AN RGS21 MODULATOR, AND METHODS OF USE THEREOF TO MODULATE TASTE SENSATION

CROSS REFERENCE TO RELATED APPLICATION

This application claims the priority benefit of U.S. Provisional Application No. 60/820,426, filed Jul. 26, 2006, the contents of which are hereby incorporated in their entirety.

BACKGROUND OF THE INVENTION

1. Field of the Invention

The present invention relates to methods for identifying modulators of a regulator of G-protein signaling (RGS) protein. The present invention also relates to compositions comprising an RGS modulatory compound, and to methods of using such compositions to modulate G protein-coupled receptor (GPCR) signal transduction. In particular, the present invention relates to methods for identifying compounds that specifically inhibit or enhance the activity of an RGS21 protein or biologically active fragment thereof, compositions comprising such a compound; and methods of using such a compound to modulate taste signal transduction through GPCR taste signal transduction processes.

2. Background

G protein-coupled receptors (GPCRs) play a major role in signal transduction and are targets of many therapeutic drugs. It has been reported for a long time that the standard model of GPCR signal transduction is restricted to a three-component system: G-protein coupled receptor (GPCR), G protein, and effector (Neubig and Siderovski, 2002, Nat. Rev. Drug Discov. 1(3):187-97). GPCRs are cell-surface receptor proteins having seven transmembrane domains. Each G protein is a membrane-associated heterotrimeric complex that comprises a GTP-hydrolysing Gα subunit and a Gβγ dimeric subunit. Gα subunits are molecular switches that control a broad range of physiological processes in cells. Gα subunits exist in an inactive, GDP-bound state or in an activated, GTP-bound state where they interact with downstream signaling proteins to elicit a specific signaling response (FIG. 1). The activation and inactivation of Gα proteins are regulated by ligand-bound GPCRs and GTPase accelerating proteins (GAPs), respectively. GPCRs promote cell signaling, upon binding to a ligand, by catalyzing the exchange of guanosine tri-phosphate (GTP) for guanosine di-phosphate (GDP) onto the α subunit of heterotrimeric G proteins. GAPs bind to the active, GTP-bound form of the Gα protein and stimulate the G protein's intrinsic GTPase activity, whereby the terminal phosphate residue of the bound GTP is hydrolyzed to GDP, thus returning the Gα protein to the inactive state (FIG. 1).

When an agonist binds to a GPCR, it causes conformational changes that enhance the guanine-nucleotide-exchange activity of the GPCR, leading to the release of GDP (and subsequent binding to GTP) by the Gα subunit. On binding to GTP, conformational changes within the three 'switch' regions of the Cα subunit allow the release of the Gβγ subunits and the subsequent engagement of effectors that are specific to each Gα subtype. Freed Gβγ subunits also can modulate effectors, including ion channels and specific isoforms of adenylyl cyclase and phospholipase (PLC) (Neubig and Siderovski, 2002, Nat. Rev. Drug Discov. 1(3):187-97, FIG. 1 and Table 1).

Recently, a protein family has been discovered that acts as a new component of GPCR signal transduction. This protein family consists of proteins known as regulator of G protein signaling (RGS) proteins (DeVries et al., 2000, Ann. Rev. Pharmacol. 40:235; Ross and Wilkie, 2001, Ann. Rev. Biochem. 69:795). RGS proteins strongly modulate the activity of G proteins and play a key role in GPCR signal transduction. Their best-known function is to act as a GTPase activating protein (GAP), inhibiting G protein signaling by accelerating GTP hydrolysis, and thus turning off G protein signals. In particular, RGS proteins control the output of signaling by an activated Gα subunit by directly binding to the GTP-bound Gα subunit. This binding markedly accelerates the subunit's rate of GTP hydrolysis, and therefore, the rate of inactivation of GPCR signaling (Neubig and Siderovski, 2002, Nat. Rev. Drug Discov. 1(3):187-97; Berman et al., 1996, Cell 86: 445-52; Hunt et al., 1996, Nature 383:175-77; Watson et al., 1996, Nature 383:172-75).

There are at least 37 RGS proteins present in the human genome, and these can be subdivided into distinct protein families which differ in the composition of their functional domains (FIG. 2). All RGS proteins contain at least one conserved domain of approximately 120 amino acids called the "RGS-box," which is responsible for the observed GAP activity of RGS proteins (FIG. 3). The RGS-box contacts the Gα switch regions to stabilize their configuration in the transition state between GTP-bound and GDP-bound forms. Because RGS proteins are highly diverse, have unique tissue distributions, and play diverse functional roles in living cells, RGS proteins typically also contain various non-RGS-box domains and motifs (e.g., GGL, DEP, DR/PH, PDZ domains, and a cysteine string motif).

RGS proteins negatively regulate GPCR signaling, and therefore, RGS proteins have been considered to be potential drug discovery targets because the inhibition of RGS-box GAP activity should lead to prolonged and enhanced signaling from agonist-bound GPCRs Neubig and Siderovski, 2002, Nat. Rev. Drug Discov. 1(3):187-97). Inhibitors of RGS proteins may enhance G protein signaling by impairing the inactivation of Gα protein. The potential therapeutic roles of RGS inhibitors include, but are not limited to, enhanced unction of endogenous neurotransmitters; enhanced function of exogenous GPCR-agonist drugs; reduced desensitization to agonist drugs; modified specificity of exogenous agonists; and blocked regulation of RGS-protein-mediated effector activity Neubig and Siderovski, 2002, Nat. Rev. Drug Discov. 1(3):187-97, Box 1; Zhong & Neubig, 2001, J. Pharmacol. Exp. Ther. 297:837-45).

Several RGS genes have been found in the central nervous system (CNS), providing potential drug targets for the clinical use of RGS inhibitors for CNS diseases, such as Alzheimer's disease, depression, epilepsy, Parkinson's disease, pain, and spasticity Neubig and Siderovski, 2002, Nat. Rev. Drug Discov. 1(3):187-97, Tables 3 and 4). However, because of the high diversity and complexity of RGS proteins, the effects of each RGS protein may depend on the function of the particular domains, including the RGS-box, non-RGS-box motifs, and/or other functional modules ((Neubig and Siderovski, 2002, Nat. Rev. Drug Discov. 1(3):187-97).

Taste cells are assembled into taste buds on the tongue surface (Lindemann, 1996, Physiol. Rev. 76:718-66). Two families of GPCRs have been identified in taste cells: the T1R family of GPCRs that mediates sweet and umami tastes, and the T2R family of GPCRs that mediate bitter tastes (Nelson et al., 2001, Cell 106:381-90; Nelson et al., 2002, Nature 416: 199-202; Li et al., 2002, Proc. Natl. Acad. Sci. USA 99:4692-96; Zhao et al., 2003, Cell 115:255-66; Adler et al., 2000, Cell 100: 693-702; Chandrashekar et al., 2000, Cell 100:703-11; Bufe et al., 2002, Nat. Genet. 32:397-401). Signaling downstream of all of these receptors has been shown to depend on the key effector enzyme of sweet, umami, and bitter taste transduction, phospholipase C subtype β2 (PLCβ2), and the trp channel subtype m5 (TRPM5) (Zhang et al., 2003, Cell 112:293-301).

Buccholtz et al. identified another ROS protein, RGS21, and demonstrated that RGS21 is specifically expressed in foliate, fungiform, and circumvallate taste bud cells, where it co-localizes with bitter receptors (T2R), umami receptors (T1R1/T1R3), sweetener receptors (T1R2/T1R3), α-gustducin, and phospholipase Cβ2 (PLCβ2). Buchholtz et al. also showed that RGS21 protein can associate with $G\alpha_{i/o/t/z}$, $G_{q/11/14}$, and α-gustducin. Sequence analysis of human RGS21 indicates that it contains a single RGS-box domain and no other functional domains. Furthermore, the sequence homology of the RGS-box of RGS21 to that of RGS2, a GAP for $G_{i/o}$, and $G_q$ proteins, further supports the possibility that RGS21 similarly regulates these G-proteins (FIG. 3). By analogy with other RGS proteins, it is likely possible, although not yet demonstrated, that RGS21 protein attenuates α-gustducin and/or other relevant Gα proteins that participate in taste cell signaling.

What is needed in the art are methods for identifying compounds that are useful for modulating taste signal transduction. Also needed are compounds that modulate taste signal transduction and methods of using such compounds for the modulation of taste signal transduction.

SUMMARY OF THE INVENTION

Whereas RGS21 protein is selectively expressed in taste tissue and is coexpressed with sweet taste signal transduction components, and whereas RGS21 protein has the potential to regulate sweet taste transduction processes, the present invention provides for the identification of compounds that regulate the activity of RGS21. The present invention also provides the use of such RGS21 regulatory compounds to enhance sweet taste or modulate the temporal profile of sweeteners when combined with carbohydrate and/or non-caloric sweeteners.

The present invention provides a method and/or biochemical assay for screening of a plurality of compounds so as to enable the discovery of enhancers and modulators of sweet-sensitive taste bud cell signaling. In particular, the present invention provides an alternate protein target in taste bud cells, independent of the sweetener receptor, for the discovery of sweetness enhancers and modulators. In one of the preferred embodiments, the present invention provides a method and/or biochemical assay for screening of a plurality of compounds that selectively and specifically interact with and inhibit the activity of RGS21 protein. RGS21 protein is a negative regulator of sweet taste signaling. Inhibition of RGS21 protein function in a defined and transient manner enhances sweet taste signaling by increasing the signaling output per activated sweetener receptor. Moreover, the enhancement of sweet-sensitive taste bud cell signaling by RGS21 protein inhibitors is relatively independent of such enhancement via positive allosteric modulation of sweetener receptor activity.

In one preferred embodiment, the present invention provides methods for screening a plurality of compounds that inhibit or enhance RGS21 gene expression in a host cell. In another preferred embodiment, the present invention provides methods for screening a plurality of compounds that inhibit or enhance RGS21 protein expression in a host cell. In yet another preferred embodiment, the present invention provides methods for screening a plurality of compounds that interfere with or promote RGS21 protein interaction with appropriate G proteins. All compounds identified by the methods of the present invention are considered to be RGS21 protein inhibitors and/or modulators if they bind to an RGS21 protein, interfere with, or enhance the interaction of the RGS21 protein with a corresponding G protein. Thus, the identified modulatory compounds result in either inhibition or enhancement of RGS21 protein activity, such as GTPase-acceleration (GAA) activity or GTPase-Activated Protein (GAP) activity, respectively, for GPCR-mediated signal transduction.

The present invention provides methods for identifying compounds that specifically modulate the activity of a Regulator of G-protein Signaling 21 (RGS21) protein, comprising providing an isolated RGS21 protein or a biologically active fragment thereof and an isolated Gα protein; combining the isolated RGS21 protein or a biologically active fragment thereof and the isolated Gα protein in the absence and presence of a test compound; determining the level of RGS21 GTPase-Activating Protein (GAP) activity on the isolated Gα protein in the absence and presence of the test compound; and identifying the test compound that modulates the level of RGS21 GAP activity. In one preferred embodiment, the present invention provides methods for recombinant expression and purification of RGS21 protein and Gα proteins in bacterial, yeast, insect and mammalian cells. Such methods comprise cloning cDNAs encoding RGS21 protein and an appropriate Gα protein, respectively, and producing recombinant cDNA encoding both RGS21 and Gα proteins. In one preferred embodiment, the appropriate Gα proteins include but are not limited to a Gαi protein selected from the group consisting of α-gustducin, Gαi1-3, Gαz, Gαo, Gαs, Gαolf, Gαt, Gαq, Gα11-14, and Gα16. In certain embodiments, the RGS21 protein, the Gα protein, or both are expressed in and purified from insect cells, yeast cells, bacterial cells, and mammalian cells. The invention provides that the proteins also may be expressed in and purified from a taste cell. In a preferred embodiment, the proteins are expressed in and purified from a human HuTu-80 cell. The invention further provides for specific recombinant constructs encoding the above proteins, as well as cellular hosts capable of expressing the recombinant constructs.

The present methods for identifying a compound that modulates RGS21 activity involve determining the level of RGS21 GAP activity in the presence and absence of the compound. The addition of purified RGS21 to a Gα protein that is bound to GTP increases the rate of GTP hydrolysis. Accordingly, the present invention provides methods for measuring GTP hydrolysis. In one of the preferred embodiments, the present invention provides hydrolysis of bound radioactive GTP, provided that the loss of radioactivity from the membrane-bound Gα protein provides a measure of GTP hydrolysis. In another preferred embodiment, the present invention provides fluorescence spectroscopy of BODIPYFL-GTP, provided that the loss of BODIPY fluorescence emission from the Gα protein upon addition of RGS21 provides a measure of GTP hydrolysis. In yet another preferred embodiment, the present invention provides a time-resolved FET assay for Gα and RGS21 interaction, provided that the modulatory compounds that inhibit the interaction of Gα and RGS21 decrease the TR-FRET signal.

The present invention provides methods of screening for a plurality of compounds that interfere with RGS21 protein interaction with an appropriate Gα protein. Such methods comprise providing a host cell that expresses the RGS21 protein or a biologically active fragment thereof and a Gα protein; contacting the host cell with a test compound; determining the level of RGS21 activity in the host cell; and identifying the compound that modulates the RGS21 activity in the cell. In a preferred embodiment, the appropriate Gα proteins include but are not limited to a Gαi protein selected from the group consisting of α-gustducin, Gαi1-3, Gαz, Gαo, Gαs, Gαolf, Gαt, Gαq, Gα11-14, and Gα16. In a preferred embodiment the host cell is a taste cell. In a more preferred embodiment, the taste cell is derived from human taste bud cells or is a model taste cell selected from the group consisting of STC-1 cells, NCI-H716 cells, or HuTu-80 cells. In other embodiments, the host cell is a bacterial, insect, yeast, or mammalian cell.

The present methods involve the determination of the effects of the modulatory compounds identified above on RGS21 GAP activity in taste cells. In preferred embodiments, a standard signaling assay that monitors the activation of the sweetener receptor is used. Such assays include but are not limited to determining: a) changes in second messengers (e.g., calcium ($Ca^{2+}$), $IP_3$, DAG, $PIP_2$, cAMP, cGMP, etc.), b) changes in protein kinase activities (e.g., PKA, PKC, GRK, ERK, Akt, Src, RTKs, etc.), c) changes in gastrointestinal peptide secretion, and/or d) changes in neurotransmitter secretion. In particular, the effects of a sweetener alone on one of these signaling 'readouts' are compared to the effects of the sweetener combined with a putative RGS21 modulatory compound. The present invention provides that an RGS21 protein inhibitor increases the observed effect of the sweetener. For instance, if the sweetener alone increases the release of intracellular calcium, then a combination of the sweetener and an RGS21 inhibitor should increase calcium release above the sweetener alone. In another preferred embodiment, the present invention also provides methods for screening for RGS21 protein inhibitors and modulators that modulate umami and bitter taste.

The present invention provides methods for identifying a compound that enhances sweet taste, comprising identifying a compound that inhibits RGS21 activity; determining the level of sweet signaling activated by a sweetener receptor with a sweetener alone, and in combination with the compound; and identifying the compound that increases the level of sweet signaling activated by said sweetener above the level detected with the sweetener alone. In a preferred embodiment, the sweetener is selected from the group consisting of a carbohydrate sweetener, synthetic high-potency sweetener, natural high-potency sweetener, polyol, and amino acid.

Moreover, the present invention provides methods to validate the effects of RGS21 modulators on human sweet taste, as well as umami and bitter taste. In one preferred embodiment, the present invention provides a comparison of the perceived sweetness of a test sweetener tasted by itself to that of a combination of a test sweetener and the RGS21 modulatory compound. The present invention provides that an RGS21 inhibitor enhances the perceived sweetness of the test sweetener, whereas the RGS21 enhancer decreases the perceived sweetness of the test sweetener.

The present invention further provides compositions for enhancing sweet taste signaling comprising inhibitors and/or modulatory compounds of RGS21 protein. The present invention also provides compositions comprising inhibitors and/or modulatory compounds of RGS21 protein for modulating other taste perception, e.g., umami and bitter taste.

DETAILED DESCRIPTION OF THE INVENTION

Figure 1:
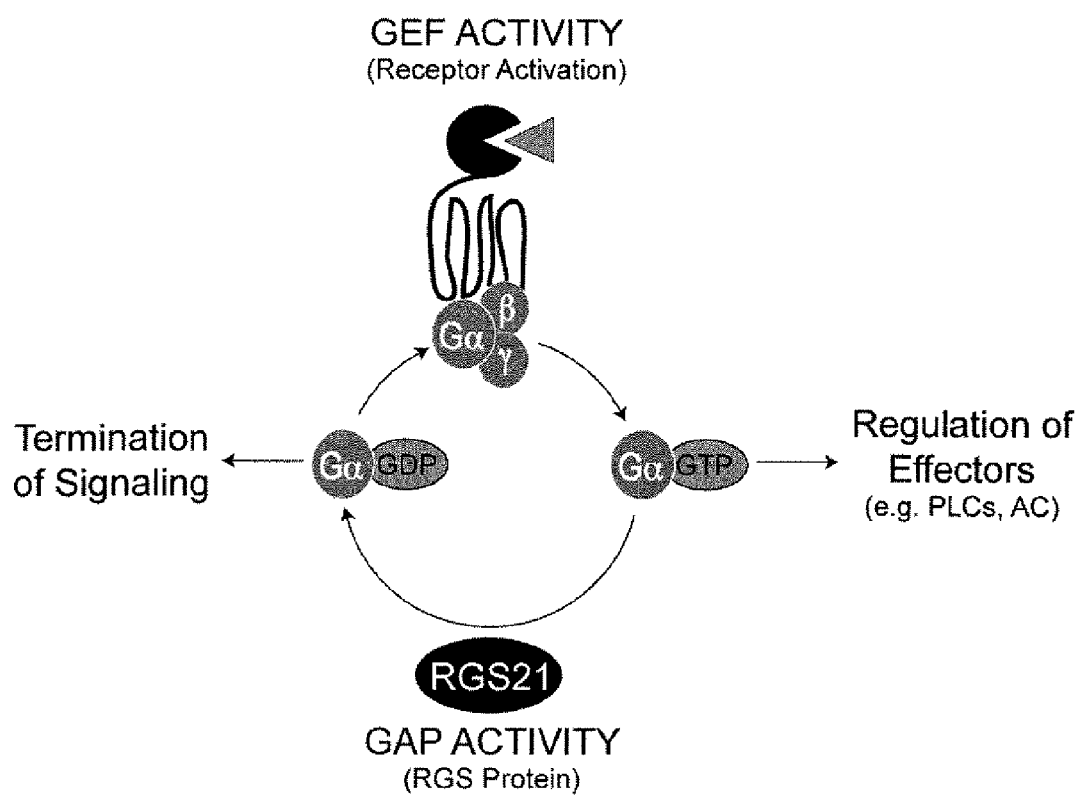
FIG. 1 illustrates regulation of heterotrimeric G protein signaling by GPCRs and the RGS21 protein. GPCRs activate Gα proteins by promoting the exchange of GDP for GTP. This stimulates downstream signaling by the Gα subunit as well as the released βγ subunits. The RGS21 protein inactivates the Gα protein by stimulating the intrinsic GTP hydrolysis activity of the Gα protein. This returns the active Gα-GTP to the inactive Gα-GDP form, which reassociates with the βγ subunit, thus, ending signaling by both entities.
Figure 2:
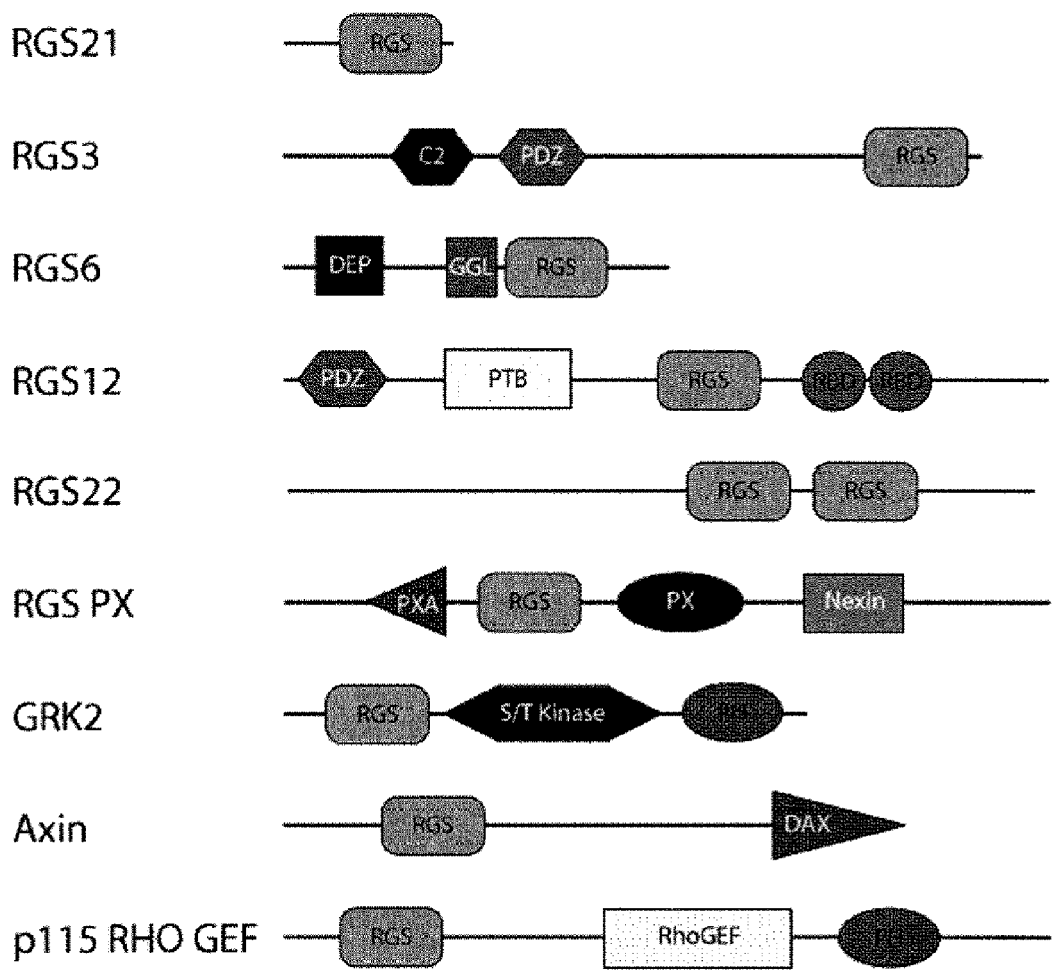
FIG. 2 illustrates the domain structure of RGS proteins. RGS proteins are subdivided into eight subclasses. All RGS proteins contain at least one conserved domain of 120 amino acids, which is referred to as the RGS box; this domain is responsible for the observed GAP activity of RGS proteins (Neubig and Siderovski, 2002, Nat. Rev. Drug Discov. 1:187-97).
Figure 3:
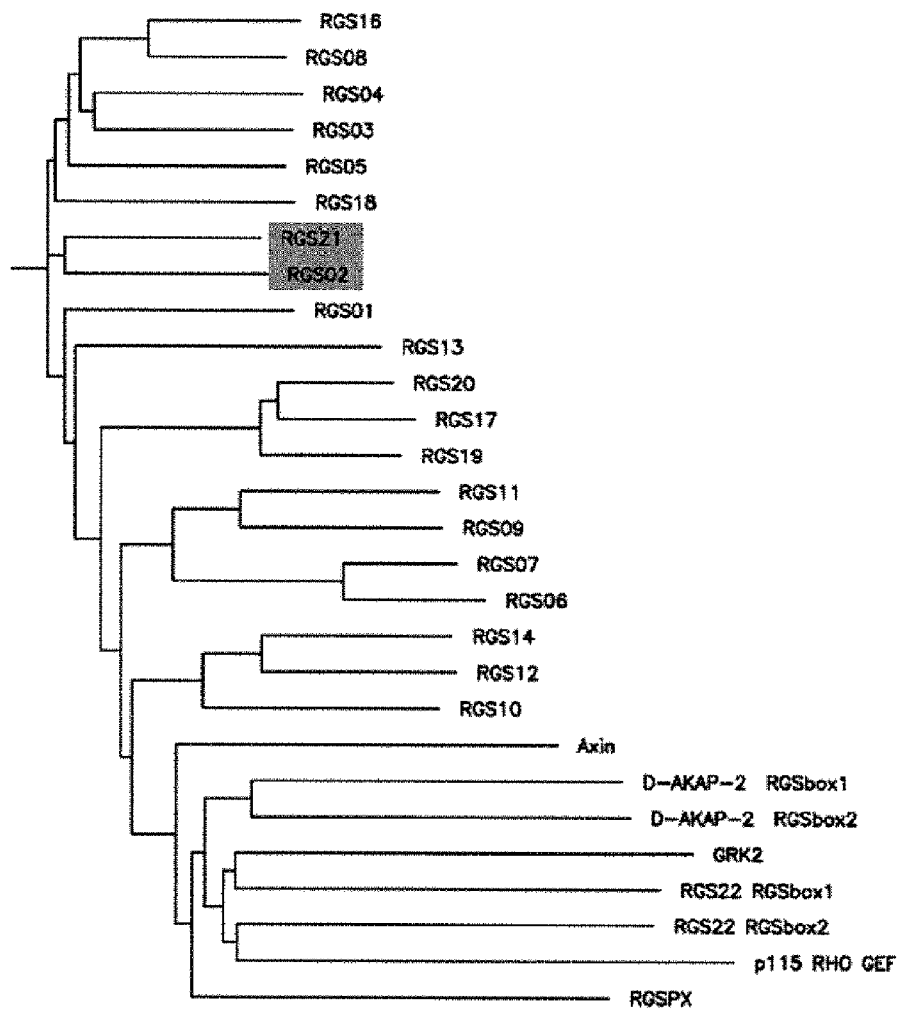
FIG. 3 is a phylogenetic tree of the RGS boxes of RGS proteins. The RGS box domains of RGS proteins were predicted using SMART software, aligned using CLUSTALW software, and the alignment was used to generate a rooted phylogenetic tree of the sequences. This figure shows that the sequence of the RGS box of RGS21 is most similar to that of RGS2, which is a GAP for Gαi, Gαo, and Gαq proteins (reviewed in Hains et al., 2004, Methods in Enz. 389:71-88). The sequence similarity between RGS2 and RGS21 supports a role for RGS21 to regulate G-protein signaling from T1R and T2R receptors coupled to Gαi family members, including gustducin and transducin.

The present invention provides methods for the identification of compounds that modulate the activity of RGS21 protein in taste cells for the purpose of modulating sweet, umami, and bitter taste through G protein coupled taste receptors. In particular, the present invention provides methods and/or biochemical assays for screening of libraries of compounds that specifically modulate RGS21 gene expression, RGS21 protein expression, and/or the interaction of RGS21 with Gα proteins, providing modulatory effects on RGS21 activity, such as RGS21 GAP activity, in taste cells, and thus, enhancing the sweet-sensitive taste cell signaling.

As used herein, the libraries of compounds are bioactive agents such as naturally-occurring compounds, biomolecules, proteins, peptides, oligopeptides, polysaccharides, nucleotides or polynucleotides. Alternatively, the compounds are small molecules. As used herein, "taste bud cells" or "taste cells" are used interchangeably that includes neuroepithelial cells that are organized into groups to form taste buds of the tongue, e.g., foliate, fungiform, and circumvallate cells (Roper et al., 1989, Ann. Rev. Neurosci. 12:329-353). Taste cells are also found in the palate and other tissues, such as the esophagus, intestine, and the stomach.

As used herein, the terms "modulatory," "modulation," "modulator," "inhibitory," "inhibiting," "inhibitors," "activating," and "activators," including their various grammatical forms, are used interchangeably to refer to modulating, inhibiting and/or activating RGS21 protein molecules e.g., ligands, agonists, antagonists, and their homologs and mimetics, that affect RGS21 genes or proteins, or fragments thereof comprising a biologically active portion. Modulators include compounds that, e.g., alter the interaction of RGS21 genes or proteins, or fragments thereof comprising a biological active portion, with Gα proteins and other effectors in GPCR signal transduction; and arresting, deactivating, and desensitizing RGS21 genes or proteins. Modulators can include genetically modified versions of RGS21 genes or proteins with altered activity, as well as naturally occurring and synthetic ligands, antagonists, agonists, small chemical molecules, and the like. "Modulatory effect" refers to up-regulation, induction, stimulation, potentiation, attenuation, and/or relief of inhibition, as well as inhibition and/or down-regulation or suppression. Inhibitors are compounds that, e.g., bind to, partially or totally block stimulation, decrease, prevent delay activation, inactivate, desensitize, or down regulate RGS21 genes or proteins, e.g., antagonists. Activators are compounds that, e.g., bind to, stimulate, increase, open, activate, facilitate, enhance activation, sensitize, or up regulate RGS21 gene or proteins, e.g., agonists.

As used herein, the term "RGS" or "RGS protein" includes regulators of G protein signaling proteins now known, or later described, which are capable of inhibiting or binding to Gαi class proteins or other Gα proteins. Such RGS proteins include, but are not limited to, GAIP, RGSz1, RGS1, RGS2, RGS3, RGS4, RGS5, RGS6, RGS7, RGS8, RGS9, RGS10, RGS11, RGS13, RGS14, RGS16, RGS17, RGS21, D-AKAP2, p115RhoGEF, PDZ-RhoGEF, bRET-RGS, Axin, and mCONDUCTIN, as well as any now known, or later described, isoforms or homologs. In addition, as used herein, the term "RGS protein" includes now known, or later described, proteins that contain an RGS core domain, including an RGS-box domain, non-RGS-box domain, or any other functional domains/motif, with or without one or more mutations, deletions, or insertions. In one preferred embodiment, the RGS protein refers to RGS21 protein, its isoforms or homologs. In yet another preferred embodiment, the RGS21 protein core domain is at least 60% homologous, preferably 75% homologous, more preferably 85%, 90%, 95%, 96%, 97%, 98%, 99% or more homologous, to a wild type RGS21 protein core domain. As used herein, the RGS21 protein core domain comprises biological active portion of the protein.

As used herein, a "biologically active portion" of an RGS protein, preferably an RGS21 protein, includes a fragment of a protein comprising amino acid sequences sufficiently homologous to, or derived from, the amino acid sequence of the protein, which includes fewer amino acids than the fall length protein, and exhibits at least one activity of the full-length protein. Typically a biologically active portion comprises a domain or motif with at least one activity of the protein. A biologically active portion of a protein can be a polypeptide which is, for example, 10, 25, 50, 100, 200, or more amino acids in length. In one embodiment, a biologically active portion of an RGS21 protein can be used as a target for developing agents which modulate RGS21 interaction with Gα proteins.

The present invention provides methods for recombinant expression and purification of RGS21 protein and corresponding and/or appropriate Gα proteins in host cells including but are not limited to bacterial, yeast, insect, and mammalian cells. In one preferred embodiment, the method starts with cloning and isolating cDNAs encoding RGS21 and appropriate Gαi proteins, respectively. The isolated cDNAs encoding RGS21 and appropriate Gαi proteins are then cloned into an expression vector, respectively, and further transformed and expressed in a host cell for producing recombinant RGS21 and Gαi proteins.

As used herein, "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. "Recombinant" also encompasses the ligation of nucleic acids having various coding regions or domains or promoter sequences from different sources into an expression cassette or vector for expression of, e.g., inducible or constitutive expression of a fusion protein comprising a translocation domain of the invention and a nucleic acid sequence amplified using a primer of the invention.

As used herein, the term "Gα" or "Gα proteins" includes all members of the Gαi class now known or later described, including but not limited to Gαi1-3, Gαz, Gαo, Gαs, Gαolf, Gαt, Gαq, Gα11-14, and Gα16. As used herein, the term "corresponding and/or appropriate Gα protein" means a Gα protein which is capable of contacting an RGS protein of interest, e.g. RGS21 protein, in the cell, screening assay, or system in use. In certain embodiments, a Gα protein may contain one or more mutations, deletions, or insertions. In such embodiments, the Gα. protein is at least 60% homologous, preferably 75% homologous, more preferably 85%, 90%, 95%, 96%, 97%, 98%, 99%, or more homologous, to a wild type Gα protein. As used herein, the term "corresponding and/or appropriate Gα protein" means a Gα protein which is capable of contacting an RGS protein, e.g. RGS21 protein, in the cell, screening assay, or system in use. More preferably, an appropriate Gα protein is capable of contacting RGS21 protein. Corresponding Gα proteins are also coupled to the GPCR and/or bound to GTP in the cell, screening assay or system in use such that the Gα protein is capable of contacting the GPCR and/or GTP, or is capable of transducing a signal in response to agonist binding to the GPCR. As used herein, the term "agonist binding to the GPCR" includes any molecule or agent which binds to GPCR and elicits a response.

As used herein, the term "cDNAs" includes DNA that is complementary to mRNA molecules present in a cell or organism mRNA that can be convened into cDNA with an enzyme such as reverse transcriptase. In one preferred embodiment, the cDNA encoding RGS21 is isolated from a human taste bud cell mRNA using an RT-PCR method well known in the at.

As used herein, the terms "polynucleotide," "nucleic acid/nucleotide," and "oligonucleotide" are used interchangeably, and include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, DNA, cDNA, genomic DNA, recombinant polynucleotides, branched polynucleotides, plasmids, vectors, isolated DNA of any sequence, isolated RNA of any sequence, nucleic acid probes, and primers. Polynucleotides may be naturally-occurring, synthetic, recombinant or any combination thereof. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form.

As used herein, the term "polynucleotide sequence" is the alphabetical representation of a polynucleotide molecule. A polynucleotide is composed of a specific sequence of four nucleotide bases: adenine (A); cytosine (C); guanine (O); thymine (T); and uracil (U) in place of thymine when the polynucleotide is RNA This alphabetical representation can be inputted into databases in a computer and used for bioinformatics applications such as, for example, functional genomics and homology searching.

As used herein, the term "isolated polynucleotide/cDNA molecule" includes polynucleotide molecules which are separated from other polynucleotide molecules which are present in the natural source of the polynucleotide. For example, with regard to genomic DNA, the term "isolated" includes polynucleotide molecules which are separated from the chromosome with which the genomic DNA is naturally associated. Preferably, an "isolated" polynucleotide is free of sequences which naturally flank the polynucleotide (i.e., sequences located at the 5' and 3' ends of the polynucleotide of interest) in the genomic DNA of the organism from which the polynucleotide is derived. For example, in various embodiments, the isolated polynucleotide molecule of the invention, or polynucleotide molecule encoding a polypeptide of the invention, can contain less than about 5 kb, 4 kb, 3 kb, 2 kb, 1 kb, 0.5 kb or 0.1 kb of nucleotide sequences which naturally flank the polynucleotide molecule in genomic DNA of the cell from which the polynucleotide is derived. Moreover, an "isolated" polynucleotide molecule, such as a cDNA molecule, can be substantially free of other cellular material, or culture medium when produced by recombinant techniques, or substantially free of chemical precursors or other chemicals when chemically synthesized.

As used herein, a "gene" includes a polynucleotide containing at least one open reading frame that is capable of encoding a particular polypeptide or protein after being transcribed and translated. Any of the polynucleotide sequences described herein may also be used to identify larger fragments or full-length coding sequences of the gene with which they are associated. Methods of isolating larger fragment sequences are known to those of skill in the art. As used herein, a "naturally-occurring" polynucleotide molecule includes, for example, an RNA or DNA molecule having a nucleotide sequence that occurs in nature (e.g., encodes a natural protein).

As used herein, the term "polypeptide" or "protein" is interchangeable, and includes a compound of two or more subunit amino acids, amino acid analogs, or peptidomimetics. The subunits may be linked by peptide bonds. In another embodiment, the subunit may be linked by other bonds, e.g., ester, ether, etc. As used herein, the term "amino acid" includes either natural and/or unnatural or synthetic amino acids, including glycine and both the D or L optical isomers, and amino acid analogs and peptidomimetics. A peptide of three or more amino acids is commonly referred to as an oligopeptide. Peptide chains of greater than three or more amino acids are referred to as a polypeptide or a protein.

In preferred embodiments, the RGS proteins used herein refer to RGS proteins that are naturally and/or recombinantly expressed in taste cells and/or host cells. More preferably, the RGS21 proteins or polynucleotides encoding RGS21 polypeptides that are naturally and/or recombinantly expressed in taste cells and/or host cells. As used herein, "express" or "expression" includes the process by which polynucleotides are transcribed into RNA and/or translated into polypeptides. If the polynucleotide is derived from genomic DNA, expression may include splicing of the RNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described below for constructing vectors in general. As used herein, the term "vector" includes a self-replicating nucleic acid molecule that transfers an inserted polynucleotide into and/or between host cells. The term is intended to include vectors that function primarily for insertion of a nucleic acid molecule into a cell, replication vectors that function primarily for the replication of nucleic acid and expression vectors that function for transcription and/or translation of the DNA or RNA. Also intended are vectors that provide more than one of the above function.

As used herein, a "host cell" is intended to include any individual cell or cell culture which can be, or has been, a recipient for vectors or for the incorporation of exogenous polynucleotides and/or polypeptides. It is also intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, including but not limited to murine, rat, simian or human cells. As used herein, a "host cell" also includes genetically modified cells. The term "genetically modified cells" includes cells containing and/or expressing a foreign or exogenous gene or polynucleotide sequence which in turn modifies the genotype or phenotype of the cell or its progeny. "Genetically modified" also includes a cell containing or expressing a gene or polynucleotide sequence which has been introduced into the cell. For example, in this embodiment, a genetically modified cell has had introduced a gene which gene is also endogenous to the cell. The term "genetically modified" also includes any addition, deletion, or disruption to a cell's endogenous nucleotides. As used herein, a "host cell" also includes taste cells. In one preferred embodiment, the taste cell is human taste cell. In a preferred embodiment, the taste cells are derived from human taste bud cells. In another preferred embodiment, the taste cells are taste cell models, such as STC-1 cells, NCI-H716 cells, or HuTu-80 cells.

More preferably, the RGS21 proteins used herein include RGS proteins encoded by polynucleotides that hybridize to the polynucleotide encoding RGS21 protein under stringent conditions. As used herein, "hybridization" includes a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Hybridization reactions can be performed under different stringent conditions. The present invention includes polynucleotides capable of hybridizing under reduced stringency conditions, more preferably stringent conditions, and most preferably highly stringent conditions, to polynucleotides encoding RGS21 protein described herein. As used herein, the term "stringent conditions" refers to hybridization overnight at 60° C. in 10×Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. As also used herein, in a preferred embodiment, the phrase "stringent conditions" refers to hybridization in a 6×SSC solution at 65° C. In another embodiment, "highly stringent conditions" refers to hybridization overnight at 65° C. in 10×Denhart's solution, 6×SSC, 0.5% SDS and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138:267-284; Current Protocols in Molecular Biology, Chapter 2, Ausubel et al., eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, N.Y., 1993. Accordingly, the RGS21 proteins encoded by nucleic acids used herein include nucleic acid having at least 60% homologous, preferably 75% homologous, more preferably 85%, more preferably 90%, most preferably 95%, 96%, 97%, 98%, 99% homologous to a polynucleotide sequence as set forth in SEQ ID NO:1 that encodes the RGS21 protein having an amino acid sequence as set forth in SEQ ID NO:2.

Moreover, the RGS21 proteins used herein can also be chimeric protein or fusion protein. As used herein, a "chimeric protein" or "fusion protein" comprises a first polypeptide operatively linked to a second polypeptide. Chimeric proteins may optionally comprise a third, fourth or fifth or other polypeptide operatively linked to a first or second polypeptide. Chimeric proteins may comprise two or more different polypeptides. Chimeric proteins may comprise multiple copies of the same polypeptide. Chimeric proteins may also comprise one or more mutations in one or more of the polypeptides. Methods for making chimeric proteins are well known in the art. In one embodiment of the present invention, the chimeric protein is a chimera of RGS21 protein with other RGS proteins. In yet another embodiment of the present invention, the chimeric protein is a chimera of Gαi and other Gα proteins.

The present invention provides methods of screening a plurality of compounds that selectively and specifically interact with RGS21 protein for modulating taste signaling. Such methods comprise isolating and purifying RGS21 protein from a host cell; determining binding of the purified RGS21 protein with test compounds in vitro; determining binding of the purified RGS21 protein with purified Gα proteins in the presence of the test compound that binds to the purified RGS21 protein; further determining RGS21 protein activity on purified Gα proteins in the presence of the test compound that binds to the purified RGS21 protein and modulates the binding of the purified RGS21 protein with purified Gα proteins; and identifying the test compound that binds to the purified RGS21 protein, changes the binding of the purified RGS21 protein with purified Gα proteins, and further modulates RGS21 protein activity. In one preferred embodiment, the RGS21 protein activity is RGS21 GAP activity.

In yet another preferred embodiment, the present invention provides methods of screening for a plurality of compounds that inhibit RGS21 gene expression in a host cell. Such methods comprise providing a host cell that selectively expresses RGS21 gene; measuring RGS21 gene expression in said host cell in the absence and presence of test compounds; and identifying a compound that inhibits RGS21 gene expression in said host cell. RGS21 gene expression can be measured using reverse transcriptase-PCR as described (von Buchholtz et al., 2004, Eur. J. Neurosci., 19, 1535-1544).

In yet another preferred embodiment, the present invention provides methods of screening for a plurality of compounds that inhibit RGS21 protein expression in a host cell. Such methods comprise providing a host cell that selectively expresses RGS21 protein; measuring RGS21 protein expression in said host cell in the absence and presence of test compounds; and identifying a compound that inhibits RGS21 protein expression in the host cell.

As used herein, an "isolated" or "purified" protein, polynucleotide or molecule means removed from the environment in which they naturally occur, or substantially free of cellular material, such as other contaminating proteins from the cell or tissue source from which the protein polynucleotide or molecule is derived, or substantially free from chemical precursors or other chemicals when chemically synthesized. The language "substantially free of cellular material" includes preparations separated from cellular components of the cells from which it is isolated or recombinantly produced or synthesized. In one embodiment, the language "substantially free of cellular material" includes preparations of a protein of interest having less than about 30% (by dry weight) of other proteins (also referred to herein as a "contaminating protein"), more preferably less than about 20%, still more preferably less than about 10%. and most preferably less than about 5% of other proteins. When the protein or polynucleotide is recombinantly produced, it is also preferably substantially free of culture medium, i.e., culture medium represents less than about 20%, more preferably less than about 10%, and most preferably less than about 5% of the volume of the preparation of the protein of interest.

The present invention further provides methods of measuring RGS21 GAP activity. As used herein, the term "GAPs" refers to GTPase Activating proteins. All RGS proteins including the RGS21 protein are GAPs for alpha subunits of the Gi and/or Gq class of heterotrimeric G proteins. The methods for measuring the RGS GAP activity are well known in the art, and it has been reported that RGS GAP activity is inhibited by phosphatidic acid (PA), lysophosphatidic acid (LPA), and phosphatidylinositol 3,4,5-trisphosphate (PIP3), but not by other phospholipids, phosphoinositides, or diacylglycerol.

In one preferred embodiment, the RGS21 GAP activity is measured in vitro by measuring the GTP hydrolysis. The present invention provides that the addition of purified RGS21 to a Gαi protein that is bound to GTP increases the rate of GTP hydrolysis. Accordingly, the present invention provides methods for measuring GTP hydrolysis in vitro. Methods for measuring GTP hydrolysis in vitro are well known in the art. In one of the preferred embodiments, the present invention provides hydrolysis of bound radioactive GTP, provided that the loss of radioactivity from the membrane-bound Gα protein provides a measure of GTP hydrolysis. In yet another preferred embodiment, the present invention provides a direct fluorescence-based assay for RGS domain GTPase accelerating activity (Willard et al., 2005, Anal Biochem. 15; 340(2):341-51). This method uses ribose-conjugated fluorescent guanine nucleotide analog BODIPYFL-GTP as a spectroscopic probe to measure intrinsic and RGS protein-catalyzed nucleotide hydrolysis by Gα (Willard et al., 2005, Anal Biochem. 15; 340(2):341-51). The present invention provides that the loss of BODIPY fluorescence emission from the Gα protein upon addition of RGS21 provides a measure of GTP hydrolysis. In yet another preferred embodiment, the present invention provides a time-resolved fluorescence resonance energy transfer (TR-FRET) assay for Gα and RGS21 interaction (Leifert et al., Anal. Biochem. in press). The TR-FRET assays represent a highly sensitive and robust high-throughput screening (HTS) method for the quantification of kinase activity (Moshinsky et al., 2003, J. Biomol. Scre. 8(4): 447-452). The present invention provides that the modulatory compounds that inhibit the interaction of Gα and RGS21 decreases the TR-FRET signal. The present invention further provides that the methods for measuring RGS21 GAP activity by measuring GTP hydrolysis are not limited to the methods presented herewith, other well known methods for measuring GTP hydrolysis are also applicable for detecting GTP hydrolysis due to RGS21 GAP activity.

The present invention further provides methods of screening for libraries of compounds that modulate RGS21 GAP activity, i.e., the present invention provides methods or screening assays for identifying modulators for RGS21 protein. The modulators for RGS21 protein include compounds or agents comprising moieties (e.g., peptides, peptidomimetics, peptoids, polynucleotides, small molecules or other drugs) which (a) bind to RGS21 gene or protein as defined above, or (b) have a modulatory effect on the interactions of the RGS21 protein with one or more of its natural substrates (e.g., Gαi), or (c) have an inhibitory effect on the expression of the RGS21 genes or proteins as defined above. Such assays typically comprise a reaction between the RGS21 genes or proteins and one or more assay components. The other components may be either the test compound itself, or a combination of test compound and a binding partner of the RGS21 gene or protein.

The test compounds of the present invention are generally either small molecules or bioactive agents. In one preferred embodiment, the test compound is a small molecule. In another preferred embodiment, the test compound is a bioactive agent. Bioactive agents include, but are not limited to, naturally-occurring or synthetic compounds or molecules ("biomolecules") having bioactivity in mammals, as well as proteins, peptides, oligopeptides, polysaccharides, nucleotides and polynucleotides. Preferably, the bioactive agent is a protein, polynucleotide or biomolecule. One skilled in the art will appreciate that the nature of the test compound may vary depending on the nature of the protein encoded by the RGS21 genes or proteins as defined above. The test compounds of the present invention may be obtained from any available source, including systematic libraries of natural and/or synthetic compounds.

In general, methods and compositions for screening for protein inhibitors or activators, and in vitro and/or in vivo protein-to-protein and protein-to-ligand binding studies are known in the art, and may be used in combination with the methods of the invention. In one embodiment, the present invention provide a method of screening for test compounds capable of inhibiting the binding of RGS21 protein and a Gα protein, by combining the test compound, isolated and/or purified RGS21 protein, and isolated and/or purified Gα protein together and determining whether binding of the RGS21 protein and Gα protein occurs and/or changes in the presence of the test compound. The test compounds may be either small molecules or bioactive agents. As discussed below, test compounds may be provided from a variety of libraries well known in the art. In yet another embodiment, the present invention provides a screening assay that involves detection of a test compound's ability to inhibit the binding of RGS21 protein to Gα protein. In yet another embodiment, inhibitors/modulators of RGS21 expression, activity or binding ability are also provided in the present invention for modulating RGS21 regulated taste signaling.

In yet another embodiment, the present invention provides a method of screening for a test compound capable of interfering with the binding of RGS21 protein and a Gα protein. The method includes combining isolated and/or purified RGS21 protein, a test compound, and an isolated and/or purified Gα protein; determining the binding of the RGS21 protein and the Gα protein; and correlating the ability of the test compound to interfere with binding, where a decrease in binding of the RGS21 protein and the Gα in the presence of the test compound as compared to the absence of the test compound indicates that the test compound is capable of inhibiting binding. In one of the preferred embodiments, a test compound is added to incubation of isolated and/or purified Gαi and RGS21 proteins, or functional fragments thereof comprising biological active portion of the protein as defined above in vitro, either simultaneously, or after equilibrium TR-FRET has been reached. The TR-FRET signal is then measured. The present invention provides that modulatory compounds that inhibit the interaction of Gα and RGS21 decrease the TR-FRET signal.

The present invention also provides methods of conducting high-throughput screening for test compounds capable of inhibiting activity or expression of RGS21 genes and/or proteins as defined above. In one embodiment, the method of high-throughput screening involves combining test compounds and RGS21 gene and/or proteins in the presence of appropriate Gα proteins and detecting the effect of the test compound on the RGS21 genes and/or proteins using the functional assays as discussed above. A variety of high-throughput functional assays well-known in the art may be used in combination to screen and/or study the reactivity of different types of activating test compounds, but since the coupling system is often difficult to predict, a number of assays may need to be configured to detect a wide range of coupling mechanisms. A variety of fluorescence-based techniques is well-known in the art and is capable of high-throughput and ultra high-throughput screening for activity. The ability to screen a large volume and a variety of test compounds with great sensitivity permits analysis of the potential RGS21 inhibitors. The present invention provides methods for high-throughput screening of test compounds for the ability to inhibit activity of RGS21 genes and/or proteins, by combining the test compounds and the gene and/or protein in high-throughput assays or in fluorescence based assays as known in the art. In one embodiment, the high-throughput screening assay detects the ability of a plurality of test compounds to bind to RGS21 genes and/or proteins. In another embodiment, the high-throughput screening assay detects the ability of a plurality of a test compound to inhibit a RGS21 protein binding partner (such as Gα protein) to bind to RGS21 protein. In yet another embodiment, the high-throughput screening assay detects the ability of a plurality of a test compounds to modulate taste signaling through taste receptor signaling transduction.

In yet another preferred embodiment, the present invention provides methods of screening for a plurality of compounds for enhancing sweet taste. Such methods comprise identifying compounds that inhibit RGS21 protein activity (RGS21 protein inhibitors); determining a sweet signaling activated by a sweetener receptor with a sweetener alone, and in combination with the compounds (RGS21 protein inhibitors); and identifying compounds (RGS21 protein inhibitors) that increase the sweet signaling of said sweetener.

The present invention further provides methods to determine the effects of modulatory compounds identified above on RGS21 GAP activity in taste cells. In preferred embodiments, standard signaling assay that monitors the activation of the sweetener receptor is used. Such measures include but are not limited to determine a) changes in second messengers (e.g., calcium, $IP_3$, DAG, $PIP_2$, cAMP, cGMP, etc.), b) changes in protein kinase activities (e.g., PKA, PKC, GRK, ERK, Akt, Src, RTKs, etc.), c) changes in sweetener receptor localization, and d) changes in taste cell membrane potential. As used herein, the "sweetener receptor" refers to now known, and later discover receptor proteins involving in the taste signaling transduction pathway, including but are not limited to the T1R family of GPCRs and the T2R family of GPCRs, their isoforms and homologs.

As used herein, the "sweetener" includes but is not limited to a) carbohydrate sweeteners including but not limited to sucrose, glucose, fructose, HFCS, HFSS, D-Tagatose, Trehalose, D-galactose, Rhamnose; b) synthetic high-potency sweeteners including but not limited to aspartame, neotame, acesulfame K, sucralose, cyclamate, saccharin, neohesperidindihydrochalcone; c) natural high-potency sweeteners including but not limited to rebaudioside A, Rebaudioside B, Rebaudioside C, Rebaudioside D, Rebaudioside E, Dulcoside A, Dulcoside B, Rubusoside, Stevioside, Mogroside IV, Mogroside V, Monatin, Curculin, Glycyrrhizin, Thaumatin, Monellin, Mabinlin, Brazzein, Monatin, Hernandulcin, Phyllodulci; d) polyols including but not limited to Erythritol, Maltitol, Mannitol, Sorbitol, Lactitol, Xylitol, Isomalt, and e) amino acids including but not limited to Glycine, D- or L-alanine, D-tryptophan, arginine, serine, threonine.

In particular, the effects of a sweetener as defined above on one of these signaling 'readouts' to the effects of the sweetener combined with a putative RGS21 modulatory compound are compared. The present invention provides that a RGS21 protein inhibitor increases the observed effect of the sweetener. For instance, if the sweetener alone increases the release of intracellular calcium, then a combination of the sweetener and an RGS21 inhibitor should increase calcium release above the sweetener alone. In another preferred embodiment, the present invention also provides methods for screening for RGS21 protein inhibitors and modulators that modulate umami and bitter taste.

Moreover, the present invention provides methods to validate in humans the effects of RGS21 modulators on human sweet taste sensation, as well as umami and bitter taste sensations. In one preferred embodiment, the present invention provides a comparison of the perceived sweetness of a test sweetener tasted by itself to that of a combination of a test sweetener and the RGS21 modulatory compound. The present invention provides that a RGS21 inhibitor enhances the perceived sweetness of the test sweetener, whereas the RGS21 enhancer decreases the perceived sweetness of the test sweetener.

Furthermore, the present invention provides a method for screening a plurality of compounds that specifically interact with and inhibit RGS21 protein in taste cells. Such method comprises: providing taste cells that naturally express one or more proteins for taste signaling comprising sweetener receptors such as T1R2/T1R3, corresponding 6-proteins containing the alpha subunit α-gustducin, effectors such as PLCβ2, and the RGS21 proteins; isolating and purifying RGS21 proteins from said taste cells; determining binding of the purified RGS21 protein with test compounds in vitro; determining binding of the purified RGS21 protein with purified Gα proteins in the presence of the test compound that binds to the purified RGS21 protein; further determining RGS21 protein activity on purified Gα proteins in the presence of the test compound that binds to the purified RGS21 protein and modulates the binding of the purified RGS21 protein with purified Gα proteins; and identifying the test compound that binds to the purified RGS21 protein, modulates the binding of the purified RGS21 protein with purified Gα proteins, and further modulates the RGS21 protein activity. In one preferred embodiment, the RGS21 protein activity is GAP activity. In another preferred embodiment, the taste cells are derived from human taste bud cells. In another preferred embodiment, the taste cells are taste cell models, such as STC-1 cells, NCI-H716 cells, or HuTu-80 cells.

The present invention further provides a composition comprising inhibitors and/or modulatory compounds of RGS21 genes and/or proteins for enhancing sweet taste signaling. The present invention also provides a composition comprising inhibitors and/or modulatory compounds of RGS21 genes and/or protein for modulating umami and bitter taste, other than just sweet taste.

These and many other variations and embodiments of the invention will be apparent to one of skill in the art upon a review of the appended description and examples.

EXAMPLES

Example 1

Recombinant Expression of RGS21 and Gα Proteins

The cDNA encoding RGS21 (GenBank Accession No. NM_001039152) is isolated from human taste bud mRNA using RT-PCR as described in von Bucholtz et. al. (2004, Eur. J. Neurosci. 19:1535-44). The cDNA sequence encoding either the full-length RGS21 protein (SEQ ID NO:1, which encodes SEQ ID NO:2) or the cDNA sequence encoding the RGS box of RGS21 (encoding amino acids at positions 21 to 137 of SEQ ID NO:2) is cloned into an appropriate vector for recombinant protein expression and purification such as an appropriate pGEX vector (GE Healthcare) as described by Willard et al. (2005, Anal. Biochem. 340:341-51). In this example, recombinant RGS21 is expressed in *E. coli* with an N-terminal glutathione S-transferase tag added to facilitate protein purification.

The cDNA encoding an appropriate $Gα_i$ protein (e.g., α-gustducin, $Gα_{i2}$, etc.) is cloned into the pPROEXHTb prokaryotic expression vector (Invitrogen, Inc.) as described by Willard et al. (2005, Anal. Biochem. 340:341-51). A cleavable hexa-histidine tag ($His_6$) is added onto the N-terminus of the Gα protein and facilitate protein purification.

BL21 bacteria are transformed with the expression plasmids described above and used to produce RGS21 and Gα proteins. The transformed bacteria are grown at 30-37° C. and incubated with isopropyl β-D-thiogalactopyranoside to induce protein expression. $His_6$-Gα proteins are purified by sequential $Ni^{2+}$-nitrilotriacetate (HiTrap Chelating HP, Amersham), anion exchange (Source 15Q, Amersham), and size exclusion chromatographies (HiPrep 26/60 Sephacryl S200, Amersham). GST-RGS21 is purified using glutathione agarose and size exclusion chromatographies (Willard et al., 2005, Anal. Biochem. 340:341-51).

The RGS21 and Gα proteins alternatively are expressed in Sf9 insect cells infected with baculovirus expression vectors (von Buchholtz et al., 2004, Eur. J. Neurosci. 19:1535-44) or in yeast cells transformed with appropriate expression plasmids (Leifert et al., 2006, Anal. Biochem. 355, 201-212). In all cases, the recombinant proteins are isolated from induced cell lysates using the chromatography schemes described above.

Example 2

In Vitro Measurement of RGS21 GAP Activity and Screening for RGS21 Modulatory Compounds The interaction of purified RGS21 with a Gα$_i$ protein that is bound to GTP increases the rate of GTP hydrolysis. GTP hydrolysis is measured using the following methods:

Method 1. Hydrolysis of Bound Radioactive GTP:

Gα GTPase activity is determined in solution as described in Snow et al. (1998, J. Biol. Chem., 273:17749-55). Briefly, GTP-loaded Gα$_{i1-3}$ and Gα$_{gustducin}$ are generated by incubating Gα proteins in the presence of [γ-$^{32}$P]-GTP (500 cpm/pmol) for 3 hours at 20° C. in the following buffer (150 μl final volume): 10 mM GTP, 5.5 mM CHAPS, 50 mM sodium HEPES, pH 7.5, 1 mM DTT, 1 mM EDTA, 0.1 mg/ml bovine serum albumin, 30 mM (NH$_2$)$_2$SO$_4$, and 4% glycerol. Following loading, reaction mixtures are exchanged by Sephadex G-25 chromatography into 1 mM CHAPS, 50 mM HEPES, pH 7.5, 1 mM DTT, 1 mM EDTA, 0.018 mg/ml bovine serum albumin. Protein eluants are then diluted 4-fold in ice-cold OG buffer (0.1% octyl glucopyranoside, 20 mM sodium HEPES pH 7.5, 80 mM NaCl, 1 mM DTT, 1 mM EDTA, 0.01 mg/ml bovine serum albumin, and 1 mM GTP).

GAP activity is initiated by adding Gα-GTP to an RGS21 protein sample in the presence or absence of a putative RGS21 modulatory compound and OG buffer (supplemented with 9 mM MgSO$_4$). Timed, 100-μl aliquots are withdrawn and quenched with 900 ml of 5% (w/v) slurry of Norit A charcoal in 50 mM NaH$_2$PO$_4$. The charcoal is pelleted, and the $^{32}$P$_i$-containing supernatant is counted. Increased $^{32}$P$_i$ in the supernatant is indicative of increased GTPase activity.

Figure 4:
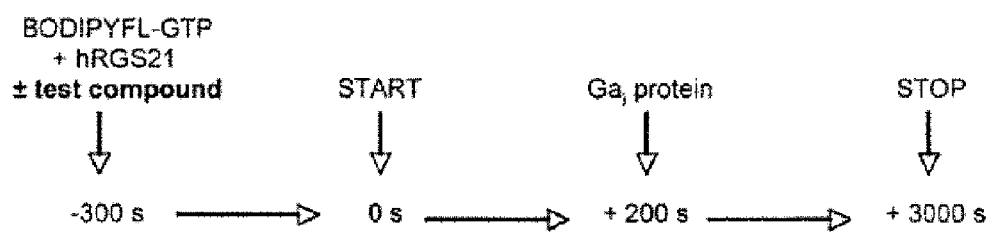
FIG. 4 illustrates a single nucleotide binding and turnover screening assay for identification of hRGS21 modulatory compounds.

Method 2. Fluorescence Spectroscopy of BODIPYFL-GTP:

BODIPYFL-GTP exhibits a 200% increase in fluorescence emission over baseline upon binding to Gα proteins whereas BODIPYFL-GDP, generated by hydrolysis, only shows a 27% increase in fluorescence emission over baseline, when bound to Gα proteins (Willard et al., 2005, Anal. Biochem. 340:341-51). The loss of BODIPY fluorescence emission from the Gα protein upon addition of RGS21 provides a measure of GTP hydrolysis. The single nucleotide binding and turnover assay format described by Willard et al. (2005, Anal. Biochem. 340:341-51) are used to screen for RGS21 modulatory compounds (FIG. 4).

Method 3. Time-Resolved FRET Assay for Gα and RGS21 Interaction:

RGS21 protein has to be physically associated with Gα$_i$ to stimulate GTPase activity (Neubig and Siderovski, 2002, Nat. Rev. Drug Discov. 1:187-97). This assay uses time-resolved FRET (TR-FRET) to monitor the physical association RGS21 and Gα proteins. His$_6$-tagged RGS21 and His$_6$-tagged Gα$_i$ proteins are fluorescently labeled using Alexa546 fluor and terbium cryptate (Tb) chelate, respectively using a five-fold molar excess of the fluor relative to the protein (Leifert et al., 2006, Anal. Biochem. 355:201-12). The recombinant RGS21 and Gαproteins, which are immobilized on Ni-NTA column, are incubated with either Alexa546 maleimide or terbium cryptate maleimide at room temperature for 2-3 hours. Following incubation, the columns containing Gα proteins are washed with buffer A (20 mM Hepes, 10 mM NaCl, 1 mM MgCl$_2$, 10 mM β-mercaptoethanol, 0.5% (w/v) polyoxyethylene-10-lauryl ether, and 10 μM GDP, pH 8.0) containing 5 mM imidazole and 300 mM NaCl (pH 8.0) to remove unbound Alexa546 or terbium. The labeled Gα proteins are eluted from the column using buffer B (20 mM Hepes, pH 8.0, 50 mM NaCl, 10 mM β-mercaptoethanol, 10 μM GDP, 1% (w/v) cholate, 50 mM MgCl$_2$, 150 mM imidazole, 10 mM NaF, and 30 μM AlCl$_3$). Elution fractions containing His$_6$-Gα proteins are pooled and dialyzed against elution buffer (20 mM Hepes, pH 8.0, 3 mM MgCl$_2$, 10 mM NaCl, 10 mM β-mercaptoethanol, 1 μM GDP, and 0.1% (w/v) cholate). The labeled His$_6$-RGS21 protein is eluted from the column with (100 mM NaCl, 300 mM imidazole, 2 mM 2-mercaptoethanol, 50 mM NaH$_2$PO$_4$, pH 6.0). Elution fractions containing His$_6$-RGS21 are pooled and dialyzed against elution buffer.

Alexa546-RGS21 is pre-incubated with a putative modulatory compound in multi-well plates (e.g., 96-well, etc.) for at least 10 minutes at room temperature. In parallel, Tb-Gα$_i$ protein is incubated with 30 μM AlCl$_3$ and 10 mM NaF in FRET buffer (50 mM Tris, pH 8.0, 100 mM NaCl, 1 mM MgCl$_2$, and 1 mM DTT) for at least 10 minutes, to form a transition state "activated" complex of Tb-Gα$_i$.GDP.AlF$_4^-$. TR-FRET reactions are initiated by mixing activated Tb-Gα$_i$.GDP.AlF$_4^-$ with Alexa546-RGS21 protein in (50 mM Tris, pH 8.0, 100 mM NaCl, 1 mM MgCl$_2$, 30 μM AlCl$_3$, 10 mM NaF, and 1 mM DTT) in a 100 μl reaction volume within a fluorescence plate reader equipped with a TR-FRET measuring system and incubated from 0-30 minutes. Time-resolved fluorometric measurements are conducted with the following instrument settings: excitation 340 nm, emission 572 nm, delay 50 μs, and counting duration 900 μs. Readings are taken until the fluorescence emission stabilized. At that time, other components such as unlabeled Gα protein or RGS21 are added, and fluorescence readings are then continued until fluorescence again is stabilized. Background fluorescence is determined by the addition of the appropriate concentration of terbium-labeled protein to incubation buffer and exposure to the same TR-FRET conditions. Background fluorescence is subtracted from all data to enable kinetic parameters to be measured. In the absence of any modulatory compounds, equilibrium binding is reached within this time frame and is observed as a plateau in the FRET signal as a function of time (Leifert et al., 2006, Anal. Biochem. 355: 201-12). The modulatory compounds that inhibit the interaction of G$_\alpha$ and RGS21 will decrease the TR-FRET signal, whereas the modulatory compounds that enhance the interaction of G$_\alpha$ and RGS21 will increase the TR-FRET signal.

Example 3

Cell-Based Assays to Identify Compounds that Modulate RGS21 Activity by Altering Taste Receptor Activation/Desensitization To determine the effects of putative RGS21 modulatory compounds in intact cells, standard signaling assays are used to monitor G-protein coupled receptor signaling including the sweetener, umami, and bitter receptors. The preferred standard signaling assay used herein may be selected from the group consisting of measures of: a) changes in second messengers (e.g., calcium (Ca$^{2+}$), cyclic nucleotides, lipid species/metabolites etc.), b) changes in protein kinase activities (e.g., PKA, PKC, GRK, MAP kinases, Akt, Src, Receptor tyrosine kinases, etc.), c) changes in taste receptor localization, and d) release of neurotransmitters (e.g., ATP, GLP-1, CCK, serotonin, PYY, etc.). These standard procedures are well known in the art, and are described in detail below. The cell-based techniques described below are applicable to cells that heterologously express recombinant T1R2 and T1R3 taste receptors (e.g., HEK293 cells, CHD cells, COS cells, BHK cells, HeLa cells, etc.) and are also applicable to cells that natively express T1R2 and T1R3 (e.g., cultured taste bud cells, mouse STC-1 enteroendocrine cells, human NCI-H716 enteroendocrine cells, and human HuTu-80 enteroendocrine cells, etc.).

The basic experimental design is to compare the effects of a sweetener on one of these signaling 'readouts' to the effects of the sweetener combined with a putative RGS21 modulatory compound. An RGS21 protein inhibitor shows an increase in the observed effect of the sweetener. For instance, if the sweetener alone increases the release of intracellular calcium, then a combination of the sweetener and an RGS21 inhibitor increases calcium release above the level seen with sweetener alone.

A. Cell-Based Assays of Intracellular Second Messengers:

Measurement of Cyclic Nucleotides:

Changes in cyclic nucleotides such as cAMP and cGMP can be measured by quantifying their amounts in cell extracts by using a commercially available non-radioactive Alphascreen cAMP assay (Perkin-Elmer). The AlphaScreen cAMP assay has been designed to directly measure levels of cAMP produced upon modulation of adenylate cyclase activity by GPCRs. The assay is based on the competition between endogenous cAMP and exogenously added biotinylated cAMP. The capture of cAMP is achieved by using a specific antibody conjugated to Acceptor beads. The assay is efficient at measuring both agonist and antagonist activities on $G\alpha i$- and $G\alpha s$-coupled GPCRs. The T1R and T2R family of GPCRs activate gustducin, which is a $G\alpha i$ family G protein.

Cells expressing a taste receptor and RGS21 (e.g., human HuTu-80 enteroendocrine cells, taste bud cells, transfected HEK cells, etc.) are plated in multi-well plates in stimulation buffer, pH 7.4 (PBS containing 0.5 mM IBMX, 5 mM HEPES, 0.1% BSA) with anti-cAMP antibody conjugated acceptor beads. The cells are then treated with an empirically-determined concentration of forskolin to produce cAMP at 50% of their maximal capacity over 30 minutes. Varying concentrations of a tastant (e.g., sucrose, aspartame, etc.) is added along with the forskolin and a putative RGS21 modulatory compound. The cells are incubated for 30 minutes in the dark and then incubated with a mixture of streptavidin-coated beads bound to biotinylated cAMP (0.25 U/µl) in cell lysis buffer for 4 hours in the dark. The fluorescence signal is measured in a Perkin-Elmer Envision plate reader. In this experimental system, increasing concentrations of tastants are expected to increase the Alphascreen signal due to inhibition of adenylyl cyclase, which decreases the cellular cAMP available for competition with the biotinylated cAMP and the anti-cAMP antibody beads.

Alternatively, the model taste cells may be stably transfected with plasmid DNA that comprises a gene encoding a transcriptional reporter protein (e.g., luciferase, β-galactosidase, etc.) under the control of a promoter sequence containing a cAMP response element (CRE). This assay monitors the transcriptional activation by the cAMP-sensitive transcription factor, cAMP response element binding protein (CREB). Therefore, the transfected cells express the transcriptional reporter protein in proportion to the amount of cAMP available in the cell. Cells expressing a taste receptor and RGS21 (e.g., human HuTu-80 enteroendocrine cells, taste bud cells, transfected HEK cells, etc.) are plated in 24-well plates and co-transfected with a CRE-luciferase (firefly) reporter plasmid (0.4 µg) and with pRL-Tk (0.1 µg), which constitutively expresses *Renilla* luciferase as a control for transfection efficiency, using Lipofectamine reagent (Invitrogen) as described (Nguyen et al., 2004, Cellular Signaling 16:1141-51; Lee et al., 2004, Mol. Endocrin. 18:1740-55). The cells are then treated with an empirically-determined concentration of forskolin in PBS containing 10 mM HEPES and 0.1% BSA, pH 7.4 to produce cAMP at 50% of their maximal capacity over 5-12 hours. Varying concentrations of a tastant (e.g., sucrose, aspartame, etc.) is added along with the forskolin and a putative RGS21 modulatory compound for 5-12 hours. The cells are solubilized, and the activities of the firefly luciferase and *Renilla* luciferase are determined using a commercially available Dual Luciferase assay kit (Promega) as per manufacturer's instructions. The firefly luciferase activity is divided by the *Renilla* luciferase activity to normalize for variations in transfection efficiency and is plotted as a function of the $\log_{10}$ of the concentration of tastant.

Measurement of Intracellular Calcium:

Changes in intracellular calcium can be measured in whole model taste cells by monitoring changes in fluorescence intensity and emission of calcium sensitive dyes (e.g., FURA-2, Fluo-3, etc.); these dyes are commercially available. Briefly, cells expressing a taste receptor and RGS21 (e.g., human HuTu-80 enteroendocrine cells, taste bud cells, transfected HEK cells, etc.) are grown in 96-well plates for 24 hours and then rinsed twice with Hanks' balanced salt solution (GIBCO-BRL) supplemented with HEPES (pH 7.4), 1.26 mM $CaCl_2$, 0.5 mM $MgCl_2$, 0.4 mM $MgSO_4$, and 0.1% BSA (referred to as $Ca^{++}$ buffer) and are incubated at 37° C. for 15 minutes in 1 ml of the same buffer with 1.0 µM fura 2-AM. Cultures are then washed three times with $Ca^{++}$ buffer, and incubated with varying concentrations of tastants (e.g., sucrose, denatonium, etc.) in the presence or absence of a putative RGS21 modulatory compound for 20 to 30 seconds prior to averaging the fluorescence responses (480-nm excitation and 535-nm emission) in a Perkin-Elmer fluorescence plate reader. The data is corrected for background fluorescence measured before compound addition, and then normalized to the response to the calcium ionophore, ionomycin (1 µM, Calbiochem).

Alternatively, changes in intracellular calcium release can be measured by transfecting cells expressing a taste receptor and RGS21 (e.g., human HuTu-80 enteroendocrine cells, taste bud cells, transfected HEK cells, etc.) with a plasmid that encodes the calcium-sensing fluorescent protein, Aequorin, whose fluorescence emission is increased upon binding to calcium in the presence of the substrate, coelenterazine. The affinity of aequorin to calcium is in the low micromolar range, and the activity of the enzyme is proportional to calcium concentration in the physiological range (50 nM to 50 µM) (Brini et al., 1995, J. Biol. Chem. 270: 9896-9903; Rizzuto et al., 1995, Biochem. Biophys. Res. Commun. 126: 1259-1268).

Measurement of Phosphoinositides by Traditional Approaches:

Sweeteners lead to the activation of the enzyme PLC-$\beta_2$ in the model taste cells. This enzyme cleaves phosphatidylinositol bisphosphate ($PIP_2$) into the second messengers, inositol trisphosphate ($IP_3$) and diacylglycerol (DAG). Changes in PIP2 can be monitored by quantifying the hydrolysis of radioactively labeled phosphoinositides using anion exchange chromatographies (Paing et al., 2002, J. Biol. Chem. 277: 1292-1300). Cells expressing a taste receptor and RGS21 (e.g., human HuTu-80 enteroendocrine cells, taste bud cells, transfected HEK cells, etc.) are labeled for 24 hours with [$^3$H]-labeled myo-D-inositol, and the cell medium is replaced with 10 mM HEPES buffer, and 20 mM lithium chloride containing 1 mg/ml BSA. Cells are then stimulated with various concentrations of tastant (over 2-3 log units) for up to 30 minutes at 37° C., extracted with 50 mM formic acid for 45 minutes at room temperature, and then neutralized with 150 mM NH$_4$OH. Cell extracts are then loaded directly on anion-exchange AG 1-X8 resin (100-200 mesh size, Bio-Rad) columns, washed with H$_2$O and then 50 mM ammonium formate, and eluted with 1.2 M ammonium formate, 0.1 M formic acid. Inositol mono-, bis-, and triphosphates eluted in this assay are quantified by scintillation counting.

Alternatively, the production of IP$_3$ can be measured using an IP$_3$ alphascreen assay, which is similar to the cAMP Alphascreen assay described above. The IP$_3$ alphascreen assay measures the ability of cellular IP$_3$, which is generated in response to sweetener receptor activation via PLC-β$_2$, to compete with biotinylated IP$_3$-beads to bind to acceptor beads that contain an IP$_3$ binding protein. Thus, increasing concentrations of sweeteners are expected to increase the cellular concentration of IP$_3$, which would then lead to a dose-dependent decrease in the alphascreen signal. Cells expressing a taste receptor and RGS21 (e.g., human HuTu-80 enteroendocrine cells, taste bud cells, transfected HEK cells, etc.) grown in 96-well plates are incubated with increasing concentrations of a tastant (e.g., sucrose, denatonium, etc.) in the presence or absence of a putative RGS21 modulatory compound for 30 seconds (in PBS Hepes pH 7.4). The cells are then lysed and incubated with the alphascreen reagents as per manufacturer's instructions, and the fluorescence signal is measured with a PerkinElmer fluorescence plate reader.

B. Cell-Based Assays of Protein Kinase Activities

Activation of the sweetener receptor has been shown to activate the serine/threonine kinases, ERKs 1 and 2, via a G$_i$ signaling pathway (Ozeck, et al., 2004, Eur. J. Pharm. 489: 139-49). In addition to the ERKs, many other kinases are also activated via G$_i$ signaling pathways including serine/threonine kinases such as Akt and receptor tyrosine kinases such as the epidermal growth factor receptor (EGF-R) tyrosine kinase. A key step in the activation of many kinases, which can be experimentally determined, is the phosphorylation of the kinase itself. The most common way to determine the extent of activation of ERK1 and 2, for instance, is to use antibodies that are specific for the phosphorylated, and hence activated, form of ERK either by immunoassays or immunoblotting methods.

Therefore, to measure the effects of sweetener receptor activation on the activity of ERK1, ERK2, Akt, MEK, and EGF-R, cell extracts from the treated model taste cells are analyzed using antibodies to the phosphorylated kinase either in a plate immunoassay or by immunoblotting. The amount of phosphorylated kinase detected in the cell extracts, prepared from the model taste cells that have been treated with a sweetener, is directly proportional to sweetener concentration. Therefore, this system also is useful to determine the effect of a putative RGS21 modulatory compound on sweetener receptor activation, by treating the model taste cells with both a sweetener and the putative RGS21 modulatory compound and then detecting the amount of phosphorylated kinase in the resultant cell extracts using antibodies specific to the phosphorylated kinase.

C. Measuring Changes in Taste Receptor Localization

Agonist stimulation of most GPCRs, such as β$_2$-adrenergic receptors, glucagon-like peptide receptors, and GABA(B) receptors, induces their internalization into cells via endocytosis (Moore et al., 2007, Annu. Rev. Physiol., 69:451-482), and receptor internalization has been widely used as a measure of receptor activation. Internalization of T1R2/T1R3 can be measured using a variety of techniques, including fluorescence microscopy-based imaging, sub-cellular fractionation of endosomes, and differential biochemical modification of cell-surface receptors (e.g., cell surface biotinylation, iodination with radioactive iodine, etc.).

Measuring Taste Receptor Localization by Fluorescence Microscopy:

As an example of a fluorescence microscopy-based imaging approach, T1R2 and/or T1R3 is fused to a fluorescent protein (e.g., green fluorescent protein (GFP), red fluorescent protein (DsRed), or any of several spectral variants of such fluorescent proteins (e.g., yellow fluorescent protein, cyan fluorescent protein, etc.)). The genetically modified T1R2/T1R3 receptor pair is then heterologously expressed in appropriate mammalian cells (e.g., HEK293, CHO, HeLa, COS, MDCK, HepG2, etc.). These cells are grown on microscope slides or coverslips and then stimulated at 37° C. from 0-3 hours with a sweetener in the presence or absence of a putative RGS21 modulatory compound. The localization of fluorescently labeled T1R2 and/or T1R3 is determined using fluorescence microscopy of either living or fixed cells. In un-stimulated cells, T1R2/T1R3 predominantly localize to the plasma membrane, which can be labeled with a variety of fluorescent dyes (e.g., FM1-43, etc.). Following sweetener stimulation, T1R2/T1R3 re-distribute to endosomes, which can be labeled with fluorescently labeled transferrin following incubation with living cells for 10-30 minutes.

Alternatively, either cell surface T1R2 and/or T1R3 is labeled with a fluorescently labeled probe (e.g., antibody, ligand, etc.). This approach is applicable to cells that heterologously express T1R2/T1R3 or to cells that naturally express T1R2/T1R3. In this case, cells are cultured on microscope slides or coverslips and incubated with the fluorescently labeled probe at 4° C. for 0-60 minutes. The cells are then warmed to 37° C. for 0-3 hours with a sweetener in the presence or absence of a putative RGS21 modulatory compound. The localization of fluorescently labeled T1R2 and/or T1R3 is determined using fluorescence microscopy (e.g., epi-fluorescence, confocal, etc.) of either living or fixed cells. In un-stimulated cells, T1R2/T1R3 predominantly localize to the plasma membrane, which can be labeled with a variety of fluorescent dyes (e.g., FM1-43, etc.). Following sweetener stimulation, T1R2/T1R3 re-distribute to endosomes, which can be labeled with fluorescently labeled transferrin following incubation with living cells for 10-30 minutes.

Measuring Taste Receptor Localization by Sub-Cellular Fractionation:

In one embodiment, T1R2/T1R3 localization to endosomes are measured using sub-cellular fractionation, where cells expressing T1R2/T1R3 (e.g., heterologous expression or native expression) are broken by mechanical shearing and separated by a combination of high and low speed centrifugation and possibly coupled to the use of a density matrix (e.g., sucrose, ficoll, etc.). Fractions are collected from the centrifugation tube and analyzed for the presence of T1R2 and/or T1R3 proteins by SDS-PAGE and immunoblotting.

Measuring Taste Receptor Localization by Differential Chemical Modification of Cell Surface Receptors:

In one embodiment, cell surface T1R2/T1R3 receptors are directly labeled with cell impermeant chemical agents (e.g., functionalized biotin cross-linking agents, radioactive iodination, labeled sweeteners, etc.), both before (time zero) and after incubation with sweeteners plus or minus a putative RGS21 modulatory compound (0-3 hours). T1R/T1R3 receptors are isolated by techniques such as immunoprecipitation, and analyzed for the abundance of labeled taste receptors. In resting cells, taste receptors will predominantly reside at the cell surface, and these cells are therefore expected to contain the greatest abundance of labeled surface taste receptors. Internalization of taste receptors upon sweetener stimulation will reduce the amount of cell surface taste receptors and the difference between the signal obtained from resting cells (time zero) and from cells treated with sweeteners provides a measure of receptor internalization.

Monitoring the Translocation of Fluorescently Labeled β-Arrestin to the Plasma Membrane:

Most GPCRs become desensitized and are incapable of stimulating further intracellular signaling (Moore et al., 2007, Annu. Rev. Physiol., 69:451-482). Two key steps promote GPCR desensitization: receptor phosphorylation and association with the multi-functional scaffolding protein, β-arrestin. In resting cells, β-arrestin predominantly resides in the cytoplasm of cell, but is translocated to the plasma membrane to associate with phosphorylated GPCRs within minutes following agonist stimulation. This translocation of β-arrestin to the plasma membrane can be visualized in cells that express fluorescently labeled β-arrestin (e.g., β-arrestin-GFP chimeric proteins). In one embodiment, cells expressing T1R2/T1R3 (e.g., HEK293 cells expressing these taste receptors, cultured taste bud cells, cultured human HuTu-80 enteroendocrine cells, etc.) are stably transfected with plasmids encoding β-arrestin-GFP. Such cells are grown on microscope slides or coverslips and stimulated with sweeteners in the presence or absence of putative RGS21 modulatory compounds for 0-3 hours. The localization of β-arrestin is determined in living or fixed cells by using fluorescence microscopy. Translocation of β-arrestin-GFP from the cytoplasm to the plasma membrane is used as a measure of sweetener receptor activation.

D. Measuring the Release of Neurotransmitters and Neuropeptides

Taste cells and other cell types such as enteroendocrine cells have been demonstrated to release neuropeptides including GLP-1, CCK, PYY, and serotonin in response to tastants; in addition to ATP. ATP secretion is quantified using a luciferin/luciferase luminescence assay system. Neuropeptide secretion is quantified using a competition ELISA/RIA approach and is described below for GLP-1 as an example.

Measurement of ATP Secretion:

The final and most important step in taste cell signaling is the release of neurotransmitters, which further stimulate afferent nerve fibers. Kinnamon and colleagues have shown that ATP is a critical 'neurotransmitter' that is secreted from taste cells and which interacts with specific purinergic, ATP-binding, receptors on nerve fibers (Finger et al., 2005, Science 310:1495-99). Cells expressing a taste receptor and RGS21 (e.g., human HuTu-80 enteroendocrine cells, taste bud cells, transfected HEK cells, etc.) are grown in 96-well plates, rinsed in PBS containing 10 mM HEPES and 0.1% BSA, pH 7.4 and stimulated with various concentrations of tastant (over 2-3 log units) in the presence and absence of a putative RGS21 modulatory compound in the same buffer for 0-30 minutes at 37° C. Samples of the culture medium of stimulated cells are collected, and the concentration of ATP is determined using commercially available luminescence assay for ATP (e.g., ATPlite assay, Perkin-Elmer).

Measurement of Gastrointestinal Peptide Secretion:

Enteroendocrine cells such as HuTu-80 cells are known to secrete gastrointestinal peptides (e.g., peptide YY (PYY), glucagon, glucagon-like peptide-1 (GLP-1), gastric insulinotropic peptide (GIP), etc.) in response to taste receptor stimulation (Rozengurt, 2006, Am. J. Physiol Gastrointest Liver Physiol. 291:G171-G177). To measure secretion of GI peptides from HuTu-80 cells, competitive ELISA or RIA can be used. As an example, secretion of GLP-1 can be measured using commercially available competitive enzymatic immunoassays (e.g., Cosmo Bio Co., Ltd.). Briefly, HuTu-80 cells are grown in multiwell dishes (e.g., 6-well, 12-well, etc.), are rinsed in PBS containing 10 mM HEPES and 0.1% BSA, pH 7.4, and stimulated with various concentrations of tastant (over 2-3 log units) in the presence and absence of a putative RGS21 modulatory compound in the same buffer for 0-30 minutes at 37° C. Samples of the culture medium of stimulated HuTu-80 cells are collected and added to 96-well plates, which are coated with goat anti-GLP-1 antibodies, along with biotinylated GLP-1 standard, and rabbit anti-GLP-1 antibodies. The plates are incubated in the dark at 4° C. overnight for 16-18 hours. The wells are rinsed with PBS, pH 7.4 and incubated with streptavidin-HRP for 1 hour at room temperature in the dark. After removing the streptavidin-HRP and rinsing with PBS, pH 7.4, o-phenylenediamine hydrochloride substrate solution is added and the reaction is developed in the dark for 30 minutes at room temperature. The reaction is stopped, and the optical absorbance of the wells is measured at 492 nm. The amount of secreted GLP-1 is determined by comparison to a standard curve, which is generated in parallel with known amounts of recombinant GLP-1.

Example 4

Use of Cell-Based Assays to Identify Compounds that Modulate RGS21 Activity by Disrupting RGS21 Protein-Protein Interactions Measurement of Interaction of Taste Receptors Gα and βγ Proteins Using FRET:

Protein-protein interactions can be monitored in living cells using fluorescence resonance energy transfer (FRET) approaches. The basis for FRET is that when two proteins, containing appropriate FRET donor and acceptor fluorophores (e.g., YFP and CFP), are bound to each other or are within 10-100 Å of each other, there is a radiative transfer of energy between fluorophores such that the emission energy from the donor fluorophore (e.g., CFP) excites the acceptor fluorophore (e.g., YFP). The result is the observation of fluorescence emission from the acceptor fluorophore (e.g., YFP) in response to excitation by the donor fluorophore (e.g., CFP). Thus, a positive FRET signal is indicative of a close interaction between two proteins. Since RGS21 must interact with an activated Gα protein to promote GTP hydrolysis, FRET can be used to monitor the interaction between RGS21 and an activated form of Gα.

In one embodiment, a pair of protein interaction partners, each bearing an appropriate fluorophore for FRET analysis (e.g., Gα-YFP+RGS21-CFP, etc.), is co-expressed in a suitable cell system (e.g., HEK293, CHO, HeLa, COS, BHK, Sf9 insect cells, yeast, etc.). Standard molecular biology methods known to one skilled in the art are used to create chimeric proteins whereby YFP is fused to $G\alpha_{gustducin}$ and CFP is fused to RGS21, and the chimeric proteins are cloned into a suitable protein expression vector (e.g., pcDNA 3.1, etc.). The pair of proteins is stably transfected into the host cells. In the case of $G\alpha_{gustducin}$-YFP+RGS21-CFP, resting cells are expected to give a low FRET signal, since $G\alpha$-$_{gustducin}$ should be in the GDP bound state and thus form an association with $G\beta_3G\gamma_{13}$ rather than an association with RGS21. Cells stimulated with either a tastant or with $AlF_4^-$, are expected to exhibit an increase in FRET signal.

Cells expressing $G\alpha_{gustducin}$-YFP+$G\beta_3$-CFP+$G\gamma_{13}$ are grown on microscope slides or multi-well dishes and are pre-incubated with a putative RGS21 modulatory compound for at least 10 minutes at 37° C. The cells are then stimulated with 30 μM $AlCl_3$ and 10 mM NaF ($AlF_4^-$) or with various concentrations of tastant (over 2-3 log units) in the presence and absence of a putative RGS21 modulatory compound. For single-cell analysis, living cells are examined in a fluorescence microscope that is equipped with appropriate optical filters to measure FRET and the FRET signal is quantified by measuring the FRET-generated fluorescence signal with a cooled CCD camera, controlled by appropriate image analysis software. For mid- to high-throughput compound screening, cells grown in multi-well dishes (e.g., 96-well, etc.), will be analyzed in a fluorescence plate reader.

Measurement of Interaction of Taste Receptors, Gα and βγ Proteins in Yeast Two-Hybrid Assays:

In another embodiment, the interaction of $G\alpha_{gustducin}$ and $G\beta_{13}\gamma_{13}$ can be measured in yeast cells using a yeast two-hybrid assay (Young et al., 2004, Methods Enzymol, 389: 277-301). In one embodiment, cDNA for RGS21 is inserted into a yeast strain (e.g., *S. cerevisiae*) that lacks the endogenous yeast RGS protein, Sst2, which normally inactivates the yeast Gα subunit, Gpa1. This strain of yeast is also engineered to express a *Renilla* luciferase reporter gene under the control of the FUS1 promoter by using molecular biology techniques that are well known to those skilled in the art. In this system, activation of the yeast pheromone signaling pathway via the yeast α-factor receptor, a GPCR, leads to the stimulation of signaling pathways, which promote the expression of the FUS1-driven luciferase protein. Comparison to the parental Sst2 deletion strain indicates the level of suppression imparted by RGS21 to blunt the de-repressed activation of luciferase observed in the parental strain upon pheromone stimulation. Thus, cells expressing RGS21 and the FUS1-luciferase DNA constructs are incubated with putative RGS21 modulatory compounds (e.g., chemical libraries, natural product libraries, etc.) and then stimulated with α-factor pheromone. Inhibitors of RGS21 are expected to relieve the inhibition of pheromone induction of luciferase.

In another embodiment, RGS21 is fused to the Gal4 transcriptional activation domain and a constitutively active mutant of $G\alpha_{gustducin}$, (Q204L), is fused to the DNA binding domain of Gal4. These DNA constructs are stably integrated into yeast strains that express a reporter gene (e.g., luciferase, β-galactosidase, CAT, etc.), whose expression is controlled by a basal promoter and several upstream Gal4 binding sites, $G\alpha_{gustducin}$ Q204L is expected to form a constitutive association with RGS21 and thus yields a high level of reporter gene activity. Therefore, any compounds that lower reporter gene activity are expected to be inhibitors of RGS21.

Example 5

Validation of Effects of RGS21 Modulatory Compounds in Human Taste Tests

The perceived intensity of a test tastant (e.g., sweetener, savory compound, or bitter, tastant) tasted by itself to that of a combination of a test tastant and the RGS21 modulatory compound is compared. A candidate RGS21 enhancer is expected to decrease the perceived intensity of the test tastant, whereas an RGS21 inhibitor is expected to enhance the perceived intensity of the test tastant. In a particular embodiment, a panel of assessors is used to measure the intensity of a test tastant solution. Briefly described, a panel of assessors (generally 8 to 12 individuals) is trained to evaluate taste intensity perception and measure intensity at several time points from when the sample is initially taken into the mouth until 3 minutes after it has been expectorated. Using statistical analysis, the results are compared between samples containing additives and samples that do not contain additives. A decrease in score for a time point measured after the sample has cleared the mouth indicates there has been a reduction in tastant perception.

The panel of assessors may be trained using procedures well known to those of ordinary skill in the art. In a particular embodiment, the panel of assessors may be trained using the SPECTRUM Descriptive Analysis Method (Meilgaard et al., Sensory Evaluation Techniques, 3rd edition, Chapter 11). Desirably, the focus of training should be the recognition of and the measure of the basic tastes; specifically, sweet, salty, sour, umami, and bitter. In order to ensure accuracy and reproducibility of results, each assessor should repeat the measure of the tastant intensity about three to about five times per sample, taking at least a five minute break between each repetition and/or sample and rinsing well with water to clear the mouth.

Generally, the method of measuring tastant intensity comprises taking a 10 mL sample into the mouth, holding the sample in the mouth for 5 seconds and gently swirling the sample in the mouth. Tastant intensity perceived is rated after 5 seconds, the sample is expectorated (without swallowing following expectorating the sample), the mouth is rinsed with one mouthful of water (e.g., vigorously moving water in mouth as if with mouth wash) and the rinse water is expectorated. The tastant intensity perceived is rated immediately upon expectorating the rinse water, waiting 45 seconds and, while waiting those 45 seconds, identifying the time of maximum perceived taste intensity and rating this intensity at that time (moving the mouth normally and swallowing as needed). Between samples, take a 5 minute break, rinsing well with water to clear the mouth.

APPENDIX

Nucleotide Sequence of RGS21 (SEQ ID NO: 1)
(GenBank Accession No. NM_001039152)

```
GGTTACCACTTGGAAAACAATTCATCTGAAAGAAGCACAGATTTTCTCAT
CTATCCTGTCAACAAAGAAAGAATCAAGAGAGCAAGGACAGTGATTTCCC
CCGCATTGCATTTGTCTTGAAGATCAGTCAGAAAGAGAAACTCGGCATCA
TCTGTGACAGACAGTGGAACGAAAAATGCCAGTGAAATGCTGTTTCTACA
GGTCACCAACTGCGGAAACAATGACATGGTCTGAAAATATGGACACGCTT
TTAGCCAACCAAGCTGGTCTAGATGCTTTTCGAATATTTCTAAAATCAGA
GTTTAGTGAAGAAAATGTTGAGTTCTGGCTTGCCTGTGAAGACTTTAAGA
AAACGAAAAATGCAGACAAAATTGCTTCCAAAGCCAAGATGATTTATTCT
GAATTCATTGAAGCTGATGCACCTAAAGAGATTAACATTGACTTCGGTAC
CAGAGACCTCATCTCAAAGAATATTGCTGAACCAACACTCAAATGCTTTG
ATGAGGCTCAGAAATTAATCTATTGTCTCATGGCCAAGGATTCTTTCCCT
CGATTTCTGAAGTCAGAGATTTATAAAAAACTGGTAAATAGCCAACAGGT
TCCAAATCATAAAAAATGGCTCCCTTTTTTGTGAGGAAGGTAAAAGTTAA
CTAATCACTATACTTCAGGGCTACAATATTTTAAATATACAAGCATGATG
CATTGTCTTTTGTTTTGTTTTTAGGATTTAGAAAACATTTTTTACCCAAA
CAGATGAATAACGTTTTATACAACAAGCCTGAATTTCTAACTCAGTTGTT
TAGAATGTATTTGCTTTACCAGCTATTTAATCTCCTACTGGGGGAGTACA
AAGAAAGTTTATAGAGATACAATATAGTCTTAAACCAAAACTGAATATTC
TTATTATATTATAATGTAAGGAATTATACACATCTTCACGTGGCAGAATG
AAAGACTTTTGAGCATCATATACACAATTTTAAATACCATTGCTTTATTC
AAAAAAATCTCACTTTTGTAAAAAGAGAATTTCTGAACCAAAATACAAGT
TTTCATTTAATATATTTAACTGTTTTTTTTCTGCCATTTCTTTCCAACTA
TTTCTAATAATGTGGTTATGAAAACTGCTACGCCTCTCAAATTATATTTT
TTAAATCACAGGAATGTATACACATTTATATGTATGTCTTGAATGCACCA
TGGACCAAAGTTTTTCAAAATATATCACTTGGCTCAATTCAATGGCATCA
CATATAAAATGTGATGAGTTATGTATGAAAAGGCCTCAAGGGTGGGGAAT
ACTGATTTTCTTATGTTAACAGAAATATAAAAGAAAGTGGAAGACTAAGG
AGCATAGATAAATCCTTATAAGATGAAGTATATAGCAAGTCATAAAATTT
AAGAATTTGCAACATTATCTACTCAATTGTGGGGAAGTATCTATTCACTC
CTTCAGCACTGATACTTGTTTATAAAACCCAAACAATTTTTAAATGCATT
TATTTTGAGATGTTCCTAAAATTGTTTCATTCTATATGTAAATATCCTGT
GATAAATACGAATAATTTCATTTCAATATGAGAAGCTGTAAAGATTCAAC
AGATCTCCCACGTTTCCATTTTCTTTGCACAGATTTATTTATCTGCATTG
ATATTTCTGCTTTTAGATTGTTTGAACATTAAAAAATGGAGGAAAAATAG
CATGGCTTATTTTATGTTTTCACAAACTACTCATTTGATAGACAAAATTT
TGTCTTCCCTTCATCATGAGAAATAAACATTTAAACATATTCAA
```

Amino Acids Sequence of RGS21 (SEQ ID NO: 2)
(GenBank Accession No. NM_001034241)

```
MPVKCCFYRS PTAETMTWSE NMDTLLANQA GLDAFRIFLK
SEFSEENVEF WLACEDFKKT KNADKIASKA KMIYSEFIEA
DAPKEINIDF GTRDLISKNI AEPTLKCFDE AQKLIYCLMA
    KDSFPRFLKS EIYKKLVNSQ QVPNHKKWLP FL
```

What is claimed is:

1. A method for identifying a compound that specifically modulates an activity of a Regulator of G-protein Signaling 21 (RGS21) protein, comprising:
   a) providing an isolated RGS21 protein or a biologically active fragment thereof, and an isolated $G_\alpha$ protein;
   b) combining and incubating the isolated RGS21 protein, or a biologically active fragment thereof, and the isolated $G_\alpha$ protein in the absence and presence of a test compound;
   c) comparing a RGS21-regulated GTPase-Activating Protein (GAP) activity in the absence and presence of the test compound; and
   d) identifying the test compound that alters the RGS21-regulated GAP activity.

2. The method of claim 1, wherein the isolated $G_\alpha$ protein is selected from the group consisting of α-gustducin, $G_{\alpha i1}$, $G_{\alpha i2}$, $G_{\alpha i3}$, $G_{\alpha z}$, $G_{\alpha o}$, $G_{\alpha s}$, $G_{\alpha olf}$, $G_{\alpha t}$, $G_{\alpha q}$, $G_{\alpha 11}$, $G_{\alpha 12}$, $G_{\alpha 13}$, $G_{\alpha 14}$, and $G_{\alpha 16}$.

3. The method of claim 1, wherein the isolated $G_\alpha$ protein is α-gustducin.

4. The method of claim 1, wherein the RGS21 protein, the $G_\alpha$ protein, or both proteins are isolated from a taste cell.

5. The method of claim 1, wherein the RGS21 protein, the $G_\alpha$ protein, or both proteins are isolated from a cell selected from the group consisting of a bacterial cell, an insect cell, a yeast cell, and a mammalian cell.

6. The method of claim 1, wherein the RGS21-regulated GAP activity is determined by measuring an amount of GTP hydrolysis, wherein the GTP is labeled with a radiolabel or a fluorescent label.

7. The method of claim 6, wherein the RGS21-regulated GAP activity is determined by measuring an amount of radiolabeled inorganic phosphate ($^{32}P_i$) released into the supernatant.

8. The method of claim 6, wherein the RGS21-regulated GAP activity is determined by fluorescence spectroscopy.

9. The method of claim 6, wherein the RGS21-regulated GAP activity is determined by a time-resolved fluorescence resonance energy transfer (TR-FRET) assay.

* * * * *

SEQUENCE LISTING

<160> NUMBER OF SEQ ID NOS: 2

<210> SEQ ID NO 1
<211> LENGTH: 1795
<212> TYPE: DNA
<213> ORGANISM: Homo sapiens

<400> SEQUENCE: 1

```
ggttaccact tggaaaacaa ttcatctgaa agaagcacag attttctcat ctatcctgtc      60
aacaaagaaa gaatcaagag agcaaggaca gtgatttccc ccgcattgca tttgtcttga     120
agatcagtca gaaagagaaa ctcggcatca tctgtgacag acagtggaac gaaaaatgcc     180
agtgaaatgc tgtttctaca ggtcaccaac tgcggaaaca atgacatggt ctgaaaatat     240
ggacacgctt ttagccaacc aagctggtct agatgctttt cgaatatttc taaaatcaga     300
gtttagtgaa gaaaatgttg agttctggct tgcctgtgaa gactttaaga aaacgaaaaa     360
tgcagacaaa attgcttcca aagccaagat gatttattct gaattcattg aagctgatgc     420
acctaaagag attaacattg acttcggtac cagagacctc atctcaaaga atattgctga     480
accaacactc aaatgctttg atgaggctca gaaattaatc tattgtctca tggccaagga     540
ttctttccct cgatttctga agtcagagat ttataaaaaa ctggtaaata gccaacaggt     600
tccaaatcat aaaaaatggc tcccttttttt gtgaggaagg taaagttaa ctaatcacta     660
tacttcaggg ctacaatatt ttaaatatac aagcatgatg cattgtcttt tgttttgttt     720
ttaggattta gaaaacattt tttacccaaa cagatgaata acgttttata caacaagcct     780
gaatttctaa ctcagttgtt tagaatgtat ttgctttacc agctatttaa tctcctactg     840
ggggagtaca agaaagtttt atagagatac aatatagtct taaaccaaaa ctgaatattc     900
ttattatatt ataatgtaag gaattataca catcttcacg tggcagaatg aaagactttt     960
gagcatcata tacacaattt taaataccat tgctttattc aaaaaaatct cacttttgta    1020
aaaagagaat ttctgaacca aaatacaagt tttcatttaa tatatttaac tgttttttt     1080
ctgccatttc tttccaacta tttctaataa tgtggttatg aaaactgcta cgcctctcaa    1140
attatatttt ttaaatcaca ggaatgtata cacatttata tgtatgtctt gaatgcacca    1200
tggaccaaag ttttttcaaaa tatatcactt ggctcaattc aatggcatca catataaaat    1260
gtgatgagtt atgtatgaaa aggcctcaag ggtggggaat actgatttttc ttatgttaac    1320
agaaatataa aagaaagtgg aagactaagg agcatagata atccttata agatgaagta     1380
tatagcaagt cataaaattt aagaatttgc aacattatct actcaattgt ggggaagtat    1440
ctattcactc cttcagcact gatacttgtt tataaaaccc aaacaatttt taaatgcatt    1500
tattttgaga tgttcctaaa attgtttcat tctatatgta aatatcctgt gataaatacg    1560
aataatttca tttcaatatg agaagctgta aagattcaac agatctccca cgtttccatt    1620
ttctttgcac agatttattt atctgcattg atatttctgc ttttagattg tttgaacatt    1680
aaaaaatgga ggaaaatag catggcttat tttatgtttt cacaaactac tcatttgata    1740
gacaaaattt tgtcttccct tcatcatgag aaataaacat ttaaacatat tcaaa        1795
```

<210> SEQ ID NO 2
<211> LENGTH: 152
<212> TYPE: PRT
<213> ORGANISM: Homo sapiens -continued

```
<400> SEQUENCE: 2

Met Pro Val Lys Cys Cys Phe Tyr Arg Ser Pro Thr Ala Glu Thr Met
1               5                   10                  15

Thr Trp Ser Glu Asn Met Asp Thr Leu Leu Ala Asn Gln Ala Gly Leu
            20                  25                  30

Asp Ala Phe Arg Ile Phe Leu Lys Ser Glu Phe Ser Glu Glu Asn Val
        35                  40                  45

Glu Phe Trp Leu Ala Cys Glu Asp Phe Lys Lys Thr Lys Asn Ala Asp
    50                  55                  60

Lys Ile Ala Ser Lys Ala Lys Met Ile Tyr Ser Glu Phe Ile Glu Ala
65                  70                  75                  80

Asp Ala Pro Lys Glu Ile Asn Ile Asp Phe Gly Thr Arg Asp Leu Ile
            85                  90                  95

Ser Lys Asn Ile Ala Glu Pro Thr Leu Lys Cys Phe Asp Glu Ala Gln
            100                 105                 110

Lys Leu Ile Tyr Cys Leu Met Ala Lys Asp Ser Phe Pro Arg Phe Leu
            115                 120                 125

Lys Ser Glu Ile Tyr Lys Lys Leu Val Asn Ser Gln Gln Val Pro Asn
            130                 135                 140

His Lys Lys Trp Leu Pro Phe Leu
145                 150
```